(12) United States Patent
Stahl et al.

(10) Patent No.: US 10,898,729 B2
(45) Date of Patent: Jan. 26, 2021

(54) SYSTEMS AND METHODS FOR INTRAFRACTIONAL CT IMAGING IN IMAGE-GUIDED RADIOTHERAPY

(71) Applicant: SHANGHAI UNITED IMAGING HEALTHCARE CO., LTD., Shanghai (CN)

(72) Inventors: Johannes Stahl, Concord, CA (US); Jonathan Maltz, Concord, CA (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 92 days.

(21) Appl. No.: 16/231,696

(22) Filed: Dec. 24, 2018

(65) Prior Publication Data

US 2019/0209868 A1 Jul. 11, 2019

Related U.S. Application Data

(63) Continuation of application No. PCT/CN2018/072226, filed on Jan. 11, 2018.

(51) Int. Cl.
*A61N 5/10* (2006.01)
*A61B 6/03* (2006.01)
*A61B 6/00* (2006.01)

(52) U.S. Cl.
CPC .......... *A61N 5/1067* (2013.01); *A61N 5/107* (2013.01); *A61N 5/1039* (2013.01);
(Continued)

(58) Field of Classification Search
None
See application file for complete search history.

(56) References Cited

U.S. PATENT DOCUMENTS 7,014,361 B1 3/2006 Ein-Gal
2008/0205588 A1* 8/2008 Kim .................. A61B 6/4447
378/20
(Continued)

FOREIGN PATENT DOCUMENTS

CN 102233158 A 11/2011
CN 106310528 A 1/2017

OTHER PUBLICATIONS

International Search Report in PCT/CN2018/072226 dated Sep. 27, 2018, 4 pages.
(Continued)

*Primary Examiner* — Hoon K Song
(74) *Attorney, Agent, or Firm* — Metis IP LLC

(57) ABSTRACT

A radiation system may include a treatment assembly including a first radiation source, a second radiation source, and a first radiation detector. The first radiation source may be configured to deliver a treatment beam covering a treatment region of the radiation system, and the treatment region may be located in a bore of the radiation system. The second radiation source may be configured to deliver a first imaging beam covering a first imaging region of the radiation system, and may be mounted rotatably on a first side of the treatment assembly. The first radiation detector may be configured to detect at least a portion of the first imaging beam, and may be mounted rotatably on a second side of the treatment assembly. The treatment assembly, the second radiation source, and the first radiation detector may be positioned such that the treatment region is addressable for the radiation system.

19 Claims, 9 Drawing Sheets

(52) U.S. Cl.
CPC ............ *A61N 5/1049* (2013.01); *A61B 6/032* (2013.01); *A61B 6/4078* (2013.01); *A61B 6/4085* (2013.01); *A61B 6/542* (2013.01); *A61N 2005/1022* (2013.01); *A61N 2005/1052* (2013.01); *A61N 2005/1061* (2013.01)

(56) References Cited

U.S. PATENT DOCUMENTS

2013/0256551 A1   10/2013  Yao
2016/0038768 A1    2/2016  Liu
2016/0303401 A1* 10/2016  Mostafavi ............ A61N 5/1049

OTHER PUBLICATIONS

Written Opinion in PCT/CN2018/072226 dated Sep. 27, 2018, 4 pages.

* cited by examiner

SYSTEMS AND METHODS FOR INTRAFRACTIONAL CT IMAGING IN IMAGE-GUIDED RADIOTHERAPY

CROSS-REFERENCE TO RELATED APPLICATIONS

This present application is a continuation of International Application No. PCT/CN2018/072226, filed on Jan. 11, 2018, the contents of which are hereby incorporated by reference.

TECHNICAL FIELD

The present disclosure generally relates to systems and methods for image-guided radiotherapy, and more specifically, relates to systems and methods for intrafractional computed tomography (CT) imaging in image-guided radiotherapy.

BACKGROUND

Image-guided radiotherapy (IGRT) is a tumor treatment technique in which three-dimensional (3D) or two-dimensional (2D) volumetric imaging (or 2D/3D imaging with time) can be used to localize a target tumor and/or tumor motion. In some IGRT applications, an object (e.g., a patient) subjected to the IGRT may need to be moved between the imaging (e.g., computed tomography [CT] imaging) position and the treatment position. The imaging operation and treatment operation may be complicated and prone to error due to, e.g., table sagging, real time change or motion of internal organs including and in the vicinity of a treatment target, or the like, or a combination thereof. Thus, it is desirable to provide systems and methods for intrafractional imaging of an object at the treatment position during a treatment process.

SUMMARY

In a first aspect of the present disclosure, a radiation system is provided. The radiation system may include a treatment assembly including a first radiation source, a second radiation source, and a first radiation detector. The first radiation source may be configured to deliver a treatment beam covering a treatment region of the radiation system, and the treatment region may be located in a bore of the radiation system. The second radiation source may be configured to deliver a first imaging beam covering a first imaging region of the radiation system, and may be mounted rotatably on a first side of the treatment assembly. The first radiation detector may be configured to detect at least a portion of the first imaging beam, and may be mounted rotatably on a second side of the treatment assembly. The treatment assembly, the second radiation source, and the first radiation detector may be positioned such that the treatment region is addressable for the radiation system.

In some embodiments, the treatment assembly may be a first ring assembly.

In some embodiments, the second radiation source may be mounted on a second ring assembly.

In some embodiments, the first radiation detector may be mounted on a third ring assembly.

In some embodiments, the first ring assembly may define a first bore, the second ring assembly may define a second bore, the third ring assembly may define a third bore, and the first bore, the second bore, and the third bore may constitute a space to receive an object.

In some embodiments, the first bore, the second bore, and the third bore may be concentric.

In some embodiments, the first radiation detector may at least partially extend into the first bore of the first ring assembly.

In some embodiments, the first radiation source may be rotatable, and a rotation of the first radiation source may be independent of at least one of the second radiation source or the first radiation detector.

In some embodiments, a rotation of the second radiation source may be independent of at least one of the first radiation source or the first radiation detector.

In some embodiments, a rotation of the first radiation detector may be independent of at least one of the first radiation source or the second radiation source.

In some embodiments, the second ring assembly may be rotatable, and a rotation of the second ring assembly may be independent of at least one of the first ring assembly or the third ring assembly.

In some embodiments, the third ring assembly may be rotatable, and a rotation of the third ring assembly may be independent of at least one of the first ring assembly or the second ring assembly.

In some embodiments, the radiation system may further include a processing module and a control module. The processing module may be configured to reconstruct an image or generate projection data based on the at least a portion of the first imaging beam detected by the first radiation detector. The control module may be configured to control operation of the radiation system.

In some embodiments, the processing module may reconstruct the image or generate the projection data when the first radiation source delivers the treatment beam.

In some embodiments, the processing module, based on the reconstructed image or projection data corresponding to the at least a portion of the first imaging beam detected by the first radiation detector, may determine an adjustment. The control module, based on the determined adjustment, may cause the first radiation source to deliver an adjusted treatment beam.

In some embodiments, the processing module, based on the reconstructed image or projection data corresponding to the at least a portion of the first imaging beam detected by the first radiation detector, may determine an adjustment. The control module, based on the determined adjustment, may cause a position of an object to be adjusted with respect to the treatment beam.

In some embodiments, the first imaging beam may include diagnostic X-rays, and the second radiation source may include a diagnostic X-ray tube.

In some embodiments, the diagnostic X-ray tube may direct the diagnostic X-rays in a substantially diagonal direction towards the first radiation detector.

In some embodiments, the second radiation source and the first radiation detector may rotate synchronously.

In some embodiments, a rotation of the second radiation source and a rotation of the first radiation detector may be synchronized mechanically, magnetically, or electrically.

In some embodiments, the second ring assembly and the third ring assembly may rotate synchronously.

In some embodiments, the rotation of the second ring assembly and the rotation of the third ring assembly may be synchronized mechanically, magnetically, or electrically.

In some embodiments, the radiation system may further include a first position sensor, configured to record a motion of the second ring assembly; a second position sensor, configured to record a motion of the third ring assembly; and a processing module configured to determine, based on the recorded motion of the second ring assembly and the recorded motion of the third ring assembly, a motion difference between the second ring assembly and the third ring assembly.

In some embodiments, the processing module may be further configured to acquire, from the first radiation detector, imaging data generated based on the first imaging beam; and process the imaging data by accounting for or compensating for the motion difference.

In some embodiments, the motion of the second ring assembly may include at least one of a rotation or a translation of the second ring assembly. The motion of the third ring assembly may include at least one of a rotation or a translation of the third ring assembly. The motion difference between the second ring assembly and the third ring assembly may include at least one of a rotational phase difference or a translational difference between the second ring assembly and the third ring assembly.

In some embodiments, the second radiation source may deliver the first imaging beam when the first radiation source delivers the treatment beam.

In some embodiments, the delivery of the treatment beam and the delivery of the first imaging beam may alternate.

In some embodiments, the second ring assembly may further include a second radiation detector.

In some embodiments, at least one of the first radiation detector or the second radiation detector may be a flat panel detector or a computed tomography detector.

In some embodiments, the second radiation source may be movable between a first position and a second position. The second radiation source at the first position may deliver the first imaging beam toward the first radiation detector in the third ring assembly. The second radiation source at the second position may deliver a second imaging beam toward the second radiation detector in the second ring assembly.

In some embodiments, a motion of the second radiation source between the first position and the second position may include at least one of a translation and a tilt.

In some embodiments, the second ring assembly may further include a third radiation source. The third radiation source may be configured to deliver a third imaging beam.

In some embodiments, the second radiation source and the third radiation source may be positioned side by side.

In some embodiments, the first imaging beam and the third imaging beam may have different energies.

In some embodiments, the third imaging beam may cover a second imaging region of the radiation system. The first imaging region may be different from the second imaging region.

In some embodiments, the third radiation source may be configured to deliver the third imaging beam toward the second radiation detector. The third radiation source and the second radiation detector may form an imaging assembly having an isocenter. The third imaging beam may pass the isocenter of the imaging assembly.

In some embodiments, the second ring assembly may further include a third radiation detector configured to detect at least a portion of the third imaging beam. The third radiation source and the third radiation detector may form an imaging assembly having an isocenter. The third imaging beam may pass through the isocenter of the imaging assembly.

In some embodiments, the second radiation detector and the third radiation detector may be positioned side by side.

In some embodiments, the third ring assembly may further include a fourth radiation source configured to deliver a fourth imaging beam covering a third imaging region of the radiation system. The first ring assembly, the second ring assembly, and the third ring assembly may be positioned such that the treatment region, the first imaging region, and the third imaging region at least partially overlap.

In some embodiments, the first imaging region and the third imaging region may overlap at a first overlapping region. The first overlapping region and the treatment region may at least partially overlap.

In some embodiments, the second ring assembly may further include a second radiation detector configured to detect at least a portion of the fourth imaging beam.

In some embodiments, the second radiation detector may be a flat panel detector or a computed tomography detector.

In some embodiments, the first radiation detector may be further configured to detect at least a portion of the fourth imaging beam.

In some embodiments, the third ring assembly may further include a fourth radiation detector configured to detect at least a portion of the fourth imaging beam.

In some embodiments, a rotation of at least one of the first radiation source, the second radiation source, or the first radiation detector may be actuated mechanically, electronically, or magnetically.

In a second aspect of the present disclosure, a method for image-guided radiotherapy is provided. The method may include positioning an object in a radiation system, the radiation system including a treatment assembly and an imaging assembly; delivering, by the imaging assembly, from a radiation source at a first side of the treatment assembly to a radiation detector at a second side the of treatment assembly, a first imaging beam to the object, wherein the second side is opposite to the first side; detecting, by the imaging assembly, at least a portion of the first imaging beam to generate a first imaging dataset; generating, based on the first imaging dataset, an image associated with the object; and delivering, by the treatment assembly and based on the image, a treatment beam toward a target portion of the object.

In some embodiments, the treatment beam and the first imaging beam may be delivered simultaneously.

In some embodiments, the delivering a treatment beam and the delivering a first imaging beam may alternate.

In some embodiments, the delivering the treatment beam toward the target portion of the object may include detecting a movement or change of the target portion of the object based on the image; and revising, based on the detected movement or change of the target portion of the object, the delivery of the treatment beam.

In some embodiments, the delivering the treatment beam toward the target portion of the object may include detecting a movement or change of the target portion of the object based on the image; and adjusting, based on the detected movement or change of the target portion of the object, a position of the target portion of the object with respect to the treatment beam.

In some embodiments, the revising the delivery of the treatment beam may include at least one of pausing the delivery, resuming the delivery, or terminating the delivery.

In some embodiments, the method may further include generating, based on the detected movement or change of the target portion of the object, a notification.

In some embodiments, the treatment assembly may include a first radiation source in a first ring assembly.

In some embodiments, the imaging assembly may include the radiation source in a second ring assembly.

In some embodiments, the imaging assembly may include the radiation detector in a third ring assembly.

In some embodiments, the second ring assembly may be located at the first side of the first ring assembly, and the third ring assembly may be located at the second side of the first ring assembly.

In some embodiments, the method may further include determining a motion difference between the second ring assembly and the third ring assembly; processing the first imaging dataset by compensating the motion difference; and reconstructing the second image based on the processed first imaging dataset.

In some embodiments, the method may further include delivering a second imaging beam to the object by the radiation source or an additional radiation source in the second ring assembly; detecting, by a second radiation detector in the second ring assembly, the second imaging beam to generate a second imaging dataset; and correcting the second image based on the second imaging dataset.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
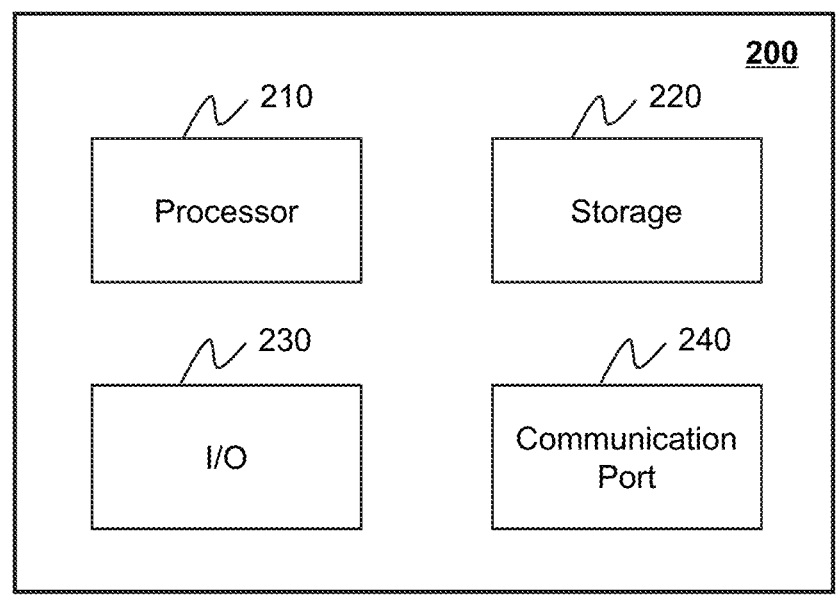
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

An aspect of the present disclosure relates to systems and methods for imaging an object during radiotherapy. With the image-guided radiotherapy device disclosed in the present disclosure, the object may be imaged and receive treatment at the same position, and need not to be moved between an imaging position and a treatment position.

Figure 1:
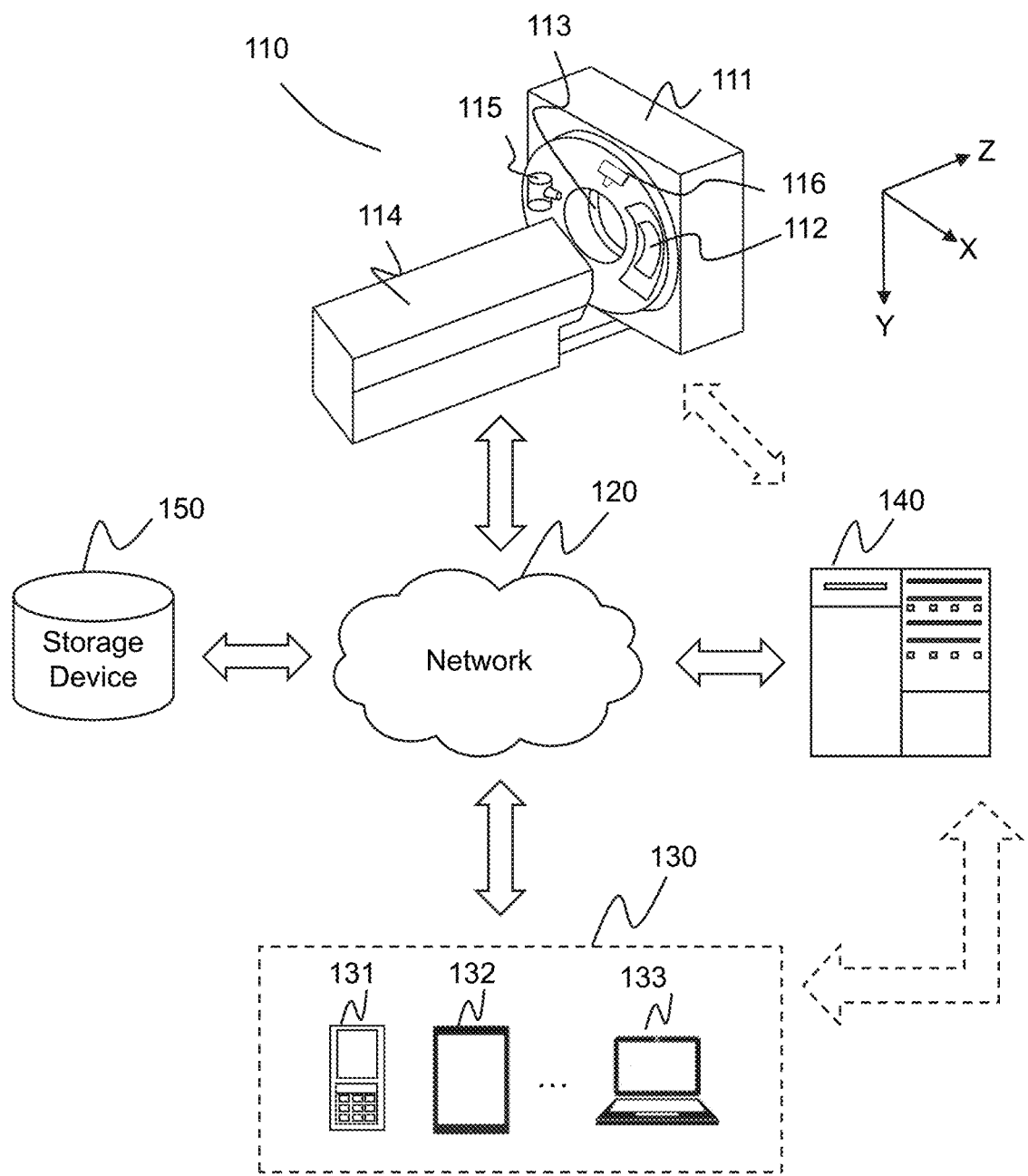
FIG. 1 is a schematic diagram illustrating an exemplary radiation system according to some embodiments of the present disclosure.

FIG. 1 is a schematic diagram illustrating an exemplary radiation system 100 according to some embodiments of the present disclosure. The radiation system 100 may include an image-guided treatment apparatus 110, a network 120, one or more terminals 130, a processing device 140, and a storage device 150.

The image-guided treatment apparatus 110 may deliver radiation toward an object (e.g., a patient or a portion thereof) based on an image of the object. A source of the radiation may emit one or more radiation rays including, for example, X-rays, α-rays, β-rays, γ-rays, etc. In some embodiments, the image of the object may be generated by an imaging device such as a computed tomography (CT) device, a magnetic resonance imaging (MRI) device, a positron emission tomography (PET) device, a single photon emission computed tomography (SPECT) device, or the like, or any combination thereof. For illustration purposes, the following descriptions are provided with reference to a CT device as the imaging device or assembly. It is understood that it is not intended to limit the scope of the present disclosure. Other imaging devices may be incorporated into the image-guided treatment apparatus 110.

The image of the object may be used to determine and/or track the location of a target region of the object. In some embodiments, the target region may be a portion of the object, for example, a head, a breast, a lung, an abdomen, a large intestine, a small intestine, a bladder, a gallbladder, a pancreas, a prostate, a uterus, an ovary, a liver, or the like, or a portion thereof, or any combination thereof. In the present disclosure, "object" and "subject" are used interchangeably. In some embodiments, the target region may include an abnormal tissue, for example, a tumor, a polyp, etc. In some embodiments, the radiation rays may be delivered toward the target region for radiotherapy based on the determined or tracked location of the target region. In some embodiments, the radiation rays for radiotherapy may be also referred to as treatment beams.

In some embodiments, the image-guided treatment apparatus 110 may include a treatment assembly (e.g., a treatment radiation source 116, an accelerator not shown in FIG. 1), an imaging assembly (e.g., one or more radiation ray emitters 115, one or more radiation ray detectors 112, etc.), a gantry assembly (e.g., the gantry 111), and an auxiliary assembly (e.g., the table 114). The gantry 111 may be configured to accommodate the treatment radiation source 116, the accelerator, the radiation ray emitters 115, the radiation ray detectors 112, etc. An object may be placed on the table 114 for treatment and/or intrafractional imaging. In some embodiments, the gantry 111 may include a bore 113 to accommodate at least a portion of the table 114 and/or the object. More descriptions of the image-guided treatment apparatus 110 may be found elsewhere in the present disclosure (e.g., FIG. 4 and the description thereof).

The network 120 may include any suitable network that can facilitate the exchange of information and/or data for the radiation system 100. In some embodiments, one or more components of the radiation system 100 (e.g., the image-guided treatment apparatus 110, the terminal(s) 130, the processing device 140, or the storage device 150) may communicate information and/or data with one or more other components of the radiation system 100 via the network 120. For example, the processing device 140 may obtain data corresponding to radiation signals from the image-guided treatment apparatus 110 via the network 120. As another example, the processing device 140 may obtain user instructions from the terminal(s) 130 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiation system 100 may be connected to the network 120 to exchange data and/or information.

The terminal 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodiments, the terminal(s) 130 may remotely operate the image-guided treatment apparatus 110. In some embodiments, the terminal(s) 130 may operate the image-guided treatment apparatus 110 via a wireless connection. In some embodiments, the terminal(s) 130 may receive information and/or instructions inputted by a user, and send the received information and/or instructions to the image-guided treatment apparatus 110 or to the processing device 140 via the network 120. In some embodiments, the terminal(s) 130 may receive data and/or information from the processing device 140. In some embodiments, the terminal(s) 130 may be part of the processing device 140. In some embodiments, the terminal(s) 130 may be omitted.

The processing device 140 may process data and/or information obtained from the image-guided treatment apparatus 110, the terminal(s) 130, and/or the storage device 150. For example, the processing device 140 may process data corresponding to radiation signals of one or more detectors obtained from the image-guided treatment apparatus 110 and reconstruct an image of the object. In some embodiments, the reconstructed image may be transmitted to the terminal(s) 130 and displayed on one or more display devices in the terminal(s) 130. In some embodiments, the processing device 140 may be a single server, or a server group. The server group may be centralized, or distributed. In some embodiments, the processing device 140 may be local or remote. For example, the processing device 140 may access information and/or data stored in the image-guided treatment apparatus 110, the terminal(s) 130, and/or the storage device 150 via the network 120. As another example, the processing device 140 may be directly connected to the image-guided treatment apparatus 110, the terminal(s) 130, and/or the storage device 150 to access stored information and/or data. As a further example, the processing device 140 may be integrated in the image-guided treatment apparatus 110. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal(s) 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the radiation system 100 (e.g., the processing device 140, the terminal(s) 130, etc.). One or more components of the radiation system 100 may access the data or instructions stored in the storage device 150 via the network 120. In some embodiments, the storage device 150 may be directly connected to or communicate with one or more components of the radiation system 100 (e.g., the processing device 140, the terminal(s) 130, etc.). In some embodiments, the storage device 150 may be part of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include, for example, routines, programs, objects, components, signals, data structures, procedures, modules, and functions, which perform particular functions described herein. For example, the processor 210 may process data obtained from the image-guided treatment apparatus 110, the terminal(s) 130, the storage device 150, and/or any other component of the radiation system 100. Specifically, the processor 210 may process one or more measured data sets obtained from the image-guided treatment apparatus 110. For example, the processor 210 may perform one-dimensional (1D) correction or two-dimensional (2D) correction for the measured data set(s). The processor 210 may reconstruct an image based on the corrected data set(s). In some embodiments, the reconstructed image may be stored in the storage device 150, the storage 220, etc. In some embodiments, the reconstructed image may be displayed on a display device by the I/O 230. In some embodiments, the processor 210 may perform instructions obtained from the terminal(s) 130. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the image-guided treatment apparatus 110, the terminal 130, the storage device 150, or any other component of the radiation system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for reducing or removing one or more artifacts in an image.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the image-guided treatment apparatus 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
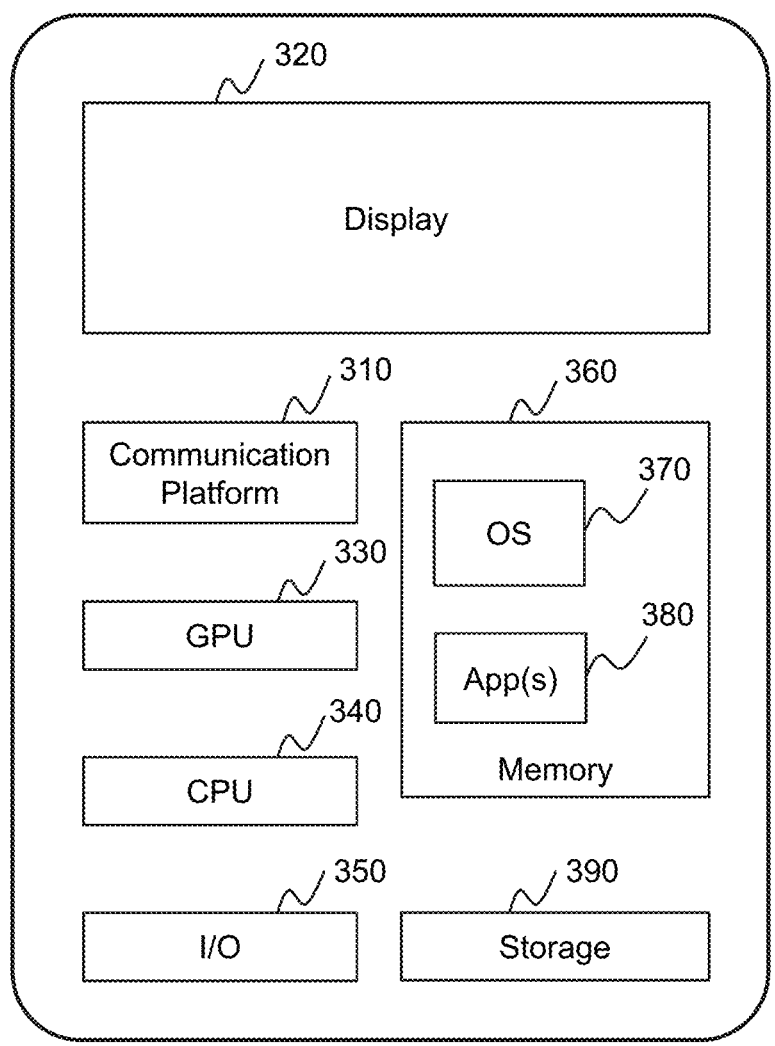
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image with reduced Nyquist ghost artifact as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 4:
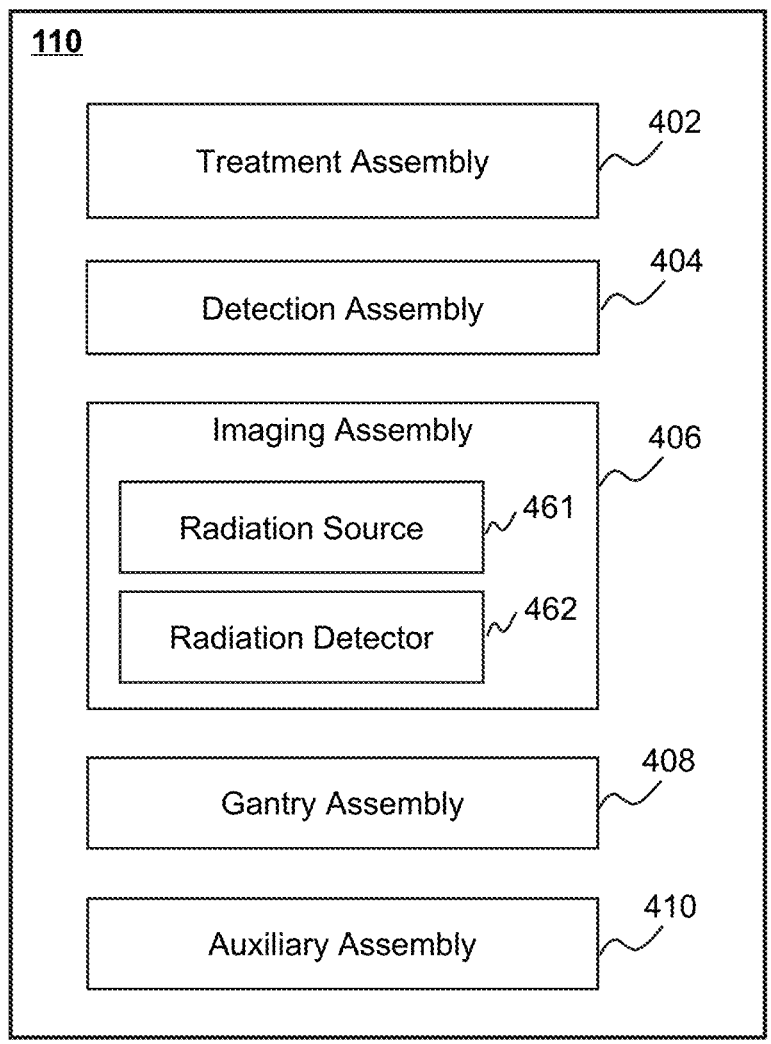
FIG. 4 is a block diagram illustrating an exemplary image-guided treatment apparatus according to some embodiments of the present disclosure.

FIG. 4 is a block diagram illustrating an exemplary image-guided treatment apparatus 110 according to some embodiments of the present disclosure. The image-guided treatment apparatus 110 may include a treatment assembly 402, a detection assembly 404, an imaging assembly 406, a gantry assembly 408, and an auxiliary assembly 410.

The treatment assembly 402 may be configured to deliver a treatment beam toward a target portion of an object (e.g., a patient). In some embodiments, the target portion may need to be subjected to radiotherapy. In some embodiments, the radiotherapy may be delivered in the form of a treatment beam. In some embodiments, the target portion may be a cell mass, a tissue, an organ (e.g., a prostate, a lung, a brain, a spine, a liver, a pancreas, a breast, etc.), or any combination thereof. In some embodiments, the target portion may be a tumor, an organ with a tumor, or a tissue with a tumor. The treatment beam may include a particle beam, a photon beam, an ultrasound beam (e.g., a high intensity focused ultrasound beam), or the like, or any combination thereof. The particle beam may include a stream of neutrons, protons, electrons, heavy ions, or the like, or any combination thereof. The photon beam may include an X-ray beam, a γ-ray beam, an α-ray beam, a β-ray beam, an ultraviolet beam, a laser beam, or the like, or any combination thereof. The shape of the X-ray beam may be a line, a narrow pencil, a narrow fan, a fan, a cone, a wedge, or the like, or any combination thereof. The energy level of the treatment beam may be suitable for radiotherapy. For example, an X-ray beam delivered by the treatment assembly 402 may have an energy of megavoltage (MV) level. Merely by way of example, the energy of the X-ray beam may be 6 MV. It should be noted that in some embodiments, one or more thermal techniques may be used to treat the target portion, and the treatment may also be image-guided.

The treatment assembly 402 may deliver the treatment beam to the target portion based on a real-time location of the target portion despite that the target portion is in motion. In some embodiments, the treatment assembly 402 may determine the delivery of the treatment beam to the target portion according to a predetermined treatment plan. The predetermined treatment plan may include a radiation dose, a radiation rate (the amount of radiation delivered per unit time, also termed the radiation output rate, or radiation monitor unit [MU] rate, and sometimes referred to as the dose rate), a radiation time, or the like, or any combination thereof. For example, the treatment assembly 402 may start the delivery of the treatment beam to the target portion when the location of the target portion is conformed to the predetermined treatment plan. In some embodiments, the treatment assembly 402 may determine the delivery of the treatment beam to the target portion according to a real-time location of the target portion. During the treatment, the motion of the target portion may be tracked and the real-time location of the target portion may be determined by the imaging assembly 406.

In some embodiments, the treatment assembly 402 may include a first radiation source, and/or a radiation source support. The first radiation source may be configured to deliver the treatment beam to the target portion. In some embodiments, the first radiation source may include a linear accelerator (linac) configured to generate the treatment beam. The radiation source support may be configured to support the first radiation source. In some embodiments, the radiation source support may include a first ring assembly made of metal, alloy, or any other suitable material. For example, the radiation source support may be made of steel, aluminum, etc. In some embodiments, the radiation source may be rotatably mounted on the radiation source support. For example, the radiation source may be rotatably mounted on an inner side of the first ring assembly.

The detection assembly 404 may be configured to detect and/or receive signals (e.g., X-ray treatment beams) emitted from the treatment assembly 402 (e.g., the first radiation source of the treatment assembly 402). The detection assembly 404 may detect and/or receive the signals emitted from the treatment assembly 402 during and/or before a radiotherapy operation performed by the treatment assembly 402. For example, during the radiotherapy operation performed by the treatment assembly 402, the detection assembly 404 may detect the signals emitted from the treatment assembly 402 and monitor the condition (e.g., the radiation dose) of the radiotherapy. As another example, before the radiotherapy operation, the treatment assembly 402 may deliver a pre-treatment beam and the detection assembly 404 may detect the pre-treatment beam for calibration (e.g., a calibration of the radiation dose).

In some embodiments, the detection assembly 404 may include a radiation detector, and/or a radiation detector support. The radiation detector may be configured to detect and/or receive the signals emitted from the treatment assembly 402. Merely by way of example, the radiation detector may be an X-ray detector. The shape of the X-ray detector may be flat, arc-shaped, circular, or the like, or any combination thereof. For example, the radiation detector may be a flat panel detector. The radiation detector support may be configured to support the radiation detector. In some embodiments, the radiation detector support may include a ring assembly made of metal, alloy, or any other suitable material. For example, the radiation detector support may be made of steel, aluminum, etc. In some embodiments, the radiation detector may be rotatably mounted on the radiation detector support. For example, the radiation detector may be rotatably mounted on an inner side of the ring assembly.

As disclosed in the present disclosure, the first radiation source of the treatment assembly 402 and the radiation detector of the detection assembly 404 may share a ring assembly. For example, the treatment assembly 402 and the detection assembly 404 may be integrated on the ring assembly. In some embodiments, the radiation detector of the detection assembly 404 may be positioned opposite to the first radiation source of the treatment assembly 402. It should be noted that in some embodiments, the first radiation source of the treatment assembly 402 and the radiation detector of the detection assembly 404 may be used as a CT imaging assembly (e.g., a cone beam CT [CBCT]). For CBCT imaging, the cone beam may have an energy of megavoltage (MV) level or kilovoltage (kV) level.

The imaging assembly 406 may be configured to perform imaging to, e.g., generate an image of the target portion, determine a real-time location of the target portion, and/or track the motion of the target portion during a radiotherapy operation performed by the treatment assembly 402. In some embodiments, the location of the target portion of the object may change with time due to various motions, for example, cardiac motion (and its effect on other organs), respiratory motion (of the lungs and/or the diaphragm, and its effect on other organs), blood flow and motion induced by vascular pulsation, muscles contracting and relaxing, secretory activity of the pancreas, or the like, or any combination thereof. The location of the target portion may be monitored based on an image (e.g., a CT image, a CBCT image, an MRI image, a PET image, a PET-CT image, etc.) of the object acquired by the imaging assembly 406 before, during, and/or after the radiotherapy operation.

In some embodiments, the imaging assembly 406 may include at least one radiation source 461 and at least one radiation detector 462. The radiation source 461 may be configured to deliver an imaging beam to the object. The imaging beam may include a particle beam, a photon beam, or the like, or any combination thereof. The particle beam may include a stream of neutrons, protons, electrons, heavy ions, or the like, or any combination thereof. The photon beam may include an X-ray beam, a γ-ray beam, an α-ray beam, a β-ray beam, an ultraviolet beam, a laser beam, or the like, or any combination thereof. The shape of the X-ray beam may be a line, a narrow pencil, a narrow fan, a fan, a cone, a wedge, a tetrahedron, or the like, or any combination thereof. For example, the radiation source may be a CBCT radiation source and the imaging beam may be a cone beam. The energy level of the imaging beam may be suitable for imaging. In some embodiments, the energy level of the imaging beam may be different from that of the treatment beam generated by the treatment assembly 402. For example, an X-ray beam delivered by the radiation source 461 may have an energy of a kilovoltage (kV) level. Merely by way of example, the energy of the X-ray beam may be 90 kVp. In some embodiments, X-rays delivered by two or more radiation sources 461 may have different energy levels.

The radiation detector 462 may be configured to detect at least a portion of the imaging beam emitted from the radiation source 461 to generate imaging data (e.g., projection data). The imaging data may be transmitted to the main processing device 140 for further processing. The processing device 140 may reconstruct an image of the object or a portion thereof based on the imaging data. The location of the target portion of the object may be determined based on the image.

In some embodiments, the radiation detector 462 may include one or more detector units. A detector unit may include a scintillator detector (e.g., a cesium iodide detector, a gadolinium oxysulfide detector), a gas detector, etc. In some embodiments, the detector units may be arranged in a single row, two rows, or any other number of rows. Merely by way of example, the radiation detector 462 may be a CT detector configured to detect X-rays. The shape of the radiation detector 462 may be flat, arc-shaped, circular, or the like, or any combination thereof. For example, the radiation detector 462 may be a flat panel detector. In some embodiments, a radiation source 461 may deliver dual energy X-rays, and accordingly, the imaging data generated by the radiation detector 462 may be amenable to processing with one or more operations suitable for tomosynthesis imaging. In some embodiments, a dual layer detector, or photon counting detector, may be employed to obtain energy information from the impinging X-ray beam.

In some embodiments, the imaging assembly 406 may include at least one support assembly. The support assembly may be a ring assembly. The at least one support assembly may be configured to support the radiation source 461 and/or the radiation detector 462. In some embodiments, the imaging assembly 406 may include a pair of the radiation source 461 and the radiation detector 462 that are located on different sides of the treatment assembly 402. In some embodiments, the imaging assembly 406 may include a pair of the radiation source 461 and the radiation detector 462 that are located on the same side of the treatment assembly 402. In some embodiments, the radiation source 461 and the radiation detector 462 may be mounted on a same ring assembly. In some embodiments, the radiation source 461 and/or the radiation detector 462 may be mounted on the same ring assembly. For example, the radiation source 461 and the radiation detector 462 may be rotatably mounted on an inner side of the same ring assembly. In some embodiments, the radiation source 461 and the radiation detector 462 may be rotatably mounted on different ring assemblies, respectively. For example, the radiation source 461 may be rotatably mounted on a second ring assembly, while the radiation detector 462 may be rotatably mounted on a third ring assembly. In some embodiments, the radiation source 461 and the radiation detector 462 may be mounted on an inner side of corresponding ring assembly (or assemblies).

In some embodiments, the first ring assembly of the treatment assembly 402 (and/or the detection assembly 404) and the second ring assembly (and/or third ring assembly) of the imaging assembly 406 may include a bore, respectively. For example, the first ring assembly may include a first bore, the second ring assembly may include a second bore, and the third ring assembly may include a third bore. The bore(s) may be configured to receive an object to be subjected to radiation in the radiation system 100. In some embodiments, one or more of the bores may share a concentric axis. More descriptions of the treatment assembly 402 and the imaging assembly 406 may be found elsewhere in the present disclosure (e.g., FIGS. 6-8 and the descriptions thereof).

The gantry assembly 408 may be configured to support one or more components of the image-guided treatment apparatus 110 (e.g., the treatment assembly 402, the detection assembly 404, the imaging assembly 406, etc.). In some embodiments, the gantry assembly 408 may include a main gantry configured to provide a main frame to support the image-guided treatment apparatus 110.

The auxiliary assembly 410 may be configured to facilitate operations of the treatment assembly 402, the detection assembly 404, the imaging assembly 406, and/or the gantry assembly 408. In some embodiments, the auxiliary assembly 410 may include a cooling assembly (not shown), a table 114 (as shown in FIG. 1), etc. The cooling assembly may be configured to produce, transfer, deliver, channel, or circulate a cooling medium to the image-guided treatment apparatus 110 to absorb heat produced by the image-guided treatment apparatus 110 (e.g., the radiation detector 462) during an imaging procedure and/or radiotherapy operation. The table 114 may be configured to support and/or transport the object (e.g., a patient) to be imaged and/or undergo radiotherapy.

It should be noted that the above description of the image-guided treatment apparatus 110 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the image-guided treatment apparatus 110 may include one or more storage devices.

Figure 5:
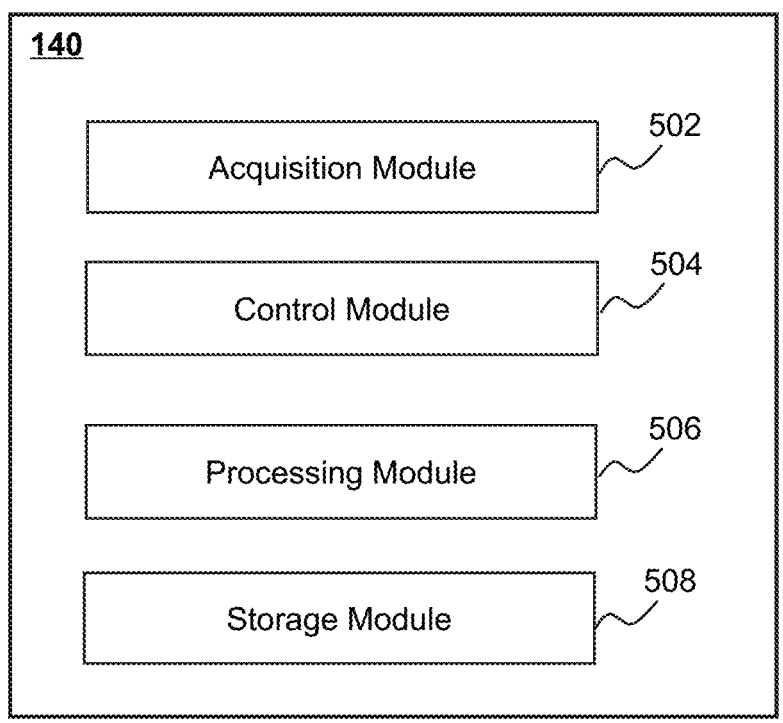
FIG. 5 is a block diagram illustrating an exemplary processing device according to some embodiments of the present disclosure.

FIG. 5 is a block diagram illustrating an exemplary processing device 140 according to some embodiments of the present disclosure. The processing device 140 may include an acquisition module 502, a control module 504, a processing module 506, and a storage module 508. At least a portion of the processing device 140 may be implemented on a computing device as illustrated in FIG. 2 or a mobile device as illustrated in FIG. 3.

The acquisition module 502 may acquire imaging data. In some embodiments, the acquisition module 502 may acquire the imaging data (e.g., CT imaging data) from the image-guided treatment apparatus 110, the terminal 130, the storage device 150, and/or an external data source (not shown). In some embodiments, the imaging data may include raw data (e.g., projection data). For example, the imaging data (e.g., projection data) may be generated based on detected imaging beams at least some of which have passed through an object being imaged and treated in the image-guided treatment apparatus 110. In some embodiments, the acquisition module 502 may acquire one or more instructions for processing the imaging data. The instructions may be executed by the processor(s) of the processing device 140 to perform exemplary methods described in this disclosure. In some embodiments, the acquired imaging data may be transmitted to the storage module 508 to be stored.

The control module 504 may control operations of the acquisition module 502, the storage module 508, the processing module 506 (e.g., by generating one or more control parameters), the image-guided treatment apparatus 110, or the like, or any combination thereof. For example, the control module 504 may cause the acquisition module 502 to acquire imaging data, the timing of the acquisition of the imaging data, etc. As another example, the control module 504 may cause the processing module 506 to process imaging data acquired by the acquisition module 502. In some embodiments, the control module 504 may control the operation of the image-guided treatment apparatus 110. For example, the control module 504 may cause the image-guided treatment apparatus 110 (e.g., the treatment assembly 402) to start, pause, stop, and/or resume the delivery of the imaging beam and/or the treatment beam to the object. As another example, the control module 504 may cause the image-guided treatment apparatus 110 to adjust the radiation dose of the imaging beam or treatment beam to the object.

In some embodiments, the control module 504 may receive a real-time instruction from an operator or retrieve a predetermined instruction provided by a user (e.g., a doctor) to control one or more operations of the image-guided treatment apparatus 110, the acquisition module 502, and/or the processing module 506. For example, the control module 504 may adjust the acquisition module 502 and/or the processing module 506 to generate one or more images of an object according to the real-time instruction and/or the predetermined instruction. As another example, the control module 504 may cause the image-guided treatment apparatus 110 to adjust the treatment beam delivered to the object according to the real-time instruction and/or the predetermined instruction. As a further example, the control module 504 may gate and/or adjust the delivery of the treatment beam of the treatment assembly 402 based on a real-time monitoring of the location of the target portion of the object according to the generated image(s). As still a further example, the control module 504 may cause the position of the table 114 and/or the treatment assembly 402 to be adjusted according to the generated image(s), so that the treatment beam may target the target portion of the object. In some embodiments, the control module 504 may communicate with one or more other modules of the processing device 140 for exchanging information and/or data.

The processing module 506 may process information provided by various modules of the processing device 140. The processing module 506 may process imaging data acquired by the acquisition module 502, imaging data retrieved from the storage module 508 and/or the storage device 150, etc. In some embodiments, the processing module 506 may reconstruct one or more images based on the imaging data according to a reconstruction technique. The reconstruction technique may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. In some embodiments, the processing module 506 may perform pre-processing on the imaging data before the reconstruction. The pre-processing may include, for example, imaging data normalization, imaging data smoothing, imaging data suppressing, imaging data encoding (or decoding), denoising, etc.

In some embodiments, the processing module 506 may analyze one or more images to determine and/or identify a region of interest (ROI) relating to the object based on an image segmentation algorithm. In some embodiments, the processing module 506 may assess and/or monitor the change of the identified ROI relating to the object. The image segmentation algorithm may include a threshold algorithm, a region growing algorithm, an algorithm based on an energy function, a level set algorithm, a region segmentation and/or merging, an edge tracking segmentation algorithm, a statistical pattern recognition algorithm, a mean clustering segmentation algorithm, a model algorithm, a segmentation algorithm based on a deformable model, an artificial neural networks algorithm, a minimum path segmentation algorithm, a tracking algorithm, a segmentation algorithm based on a rule, a coupling surface segmentation algorithm, or the like, or any combination thereof. In some embodiments, the processing module 506 may reconstruct one or more images based on one or more imaging datasets generated at different times in a radiotherapy operation. In some embodiments, based on one or more reconstructed images of an object including a target portion, the processing module 506 may determine a movement or change of the target portion.

In some embodiments, the processing module 506 may determine, based on the images and the analysis thereof, whether any change or adjustment is needed with respect to the treatment plan, and/or determine the needed adjustment. According to the determined adjustment, the control module 504 may cause the adjustment to be implemented. For instance, the control module 504 may cause the image-guided treatment apparatus 110 to deliver an adjusted treatment beam or cause a position of the object to be adjusted. For example, the processing module 506 may transmit the motion information of the target portion to the control module 504. The control module 504 may accordingly control the image-guided treatment apparatus 110 to adjust the delivery of the treatment beam by for example, pausing the delivery and/or changing the position of the source of the treatment beam. As another example, the control module 504 may accordingly control the image-guided treatment apparatus 110 to adjust the position of the object with respect to the treatment beam.

In some embodiments, the delivery of a treatment plan may be monitored and/or adjusted real time. For instance, based on the imaging data the imaging assembly 406 and/or the acquisition module 502 acquires (e.g., real time), the processing module 506 may automatically generate and/or analyze images to monitor the location of the target portion of the object, and/or assess the change of the location of the target portion, on the basis of which the processing module 506 may determine how to proceed further with the treatment plan (e.g., to continue the radiotherapy as planned, to continue the radiotherapy with a revised plan, or to terminate the radiotherapy, etc.). The processing module 506 may determine the location of the target portion based on the generated image(s). In some embodiments, the monitoring, assessment, and/or adjustment may be performed semiautomatically with the input of a user. For instance, based on the imaging data the imaging assembly 406 and/or the acquisition module 502 acquires (e.g., real time), the processing module 506 may generate one or more images and send them to be presented on a terminal 130 (e.g., a display) so that the user may analyze the images and provide an instruction as to how to proceed further with the treatment plan (e.g., to continue the radiotherapy as planned, to continue the radiotherapy with a revised plan, or to terminate the radiotherapy, etc.). As another example, based on the imaging data the imaging assembly 406 and/or the acquisition module 502 acquires (e.g., real time), the processing module 506 may generate one or more images. The processing module 506 may first analyze the images and determine if any change occurs in the target region and how much the change is. The processing module 506 may determine accordingly if any adjustment in the treatment plan is needed. If the change of the target region or the adjustment needed in the treatment plan is within a threshold, the processing module 506 may determine the adjustment automatically and send it to, e.g., the control module 504, to be implemented. In some embodiments, a notification may be generated when the processing module 506 makes such a determination. If the change of the target region or the adjustment needed in the treatment plan is not within a threshold, the processing module 506 may generate a notification to, e.g., the user (e.g., the doctor) to seek instructions from the user as to how to proceed further.

The storage module 508 may store imaging data, control parameters, processed imaging data, or the like, or a combination thereof. In some embodiments, the storage module 508 may store one or more programs and/or instructions that may be executed by the processor(s) of the processing device 140 to perform exemplary methods described in this disclosure. For example, the storage module 508 may store program(s) and/or instruction(s) that can be executed by the processor(s) of the processing device 140 to acquire imaging data of an object, reconstruct one or more images based on the imaging data, determine an ROI in the image(s), detect a movement or change of a target portion of the object based on the image(s), revise the delivery of the treatment beam to the target portion, and/or adjust the position of the object relative to the treatment beam based on the detected movement or change of the target portion.

In some embodiments, one or more modules illustrated in FIG. 5 may be implemented in at least part of the radiation system 100 as illustrated in FIG. 1. For example, the acquisition module 502, the control module 504, the processing module 506, and/or the storage module 508 may be implemented via the processing device 140 and/or the terminal 130. Via the terminal 130, a user may set parameters for scanning a subject, controlling imaging processes, adjusting parameters for reconstructing an image, etc.

Figure 6:
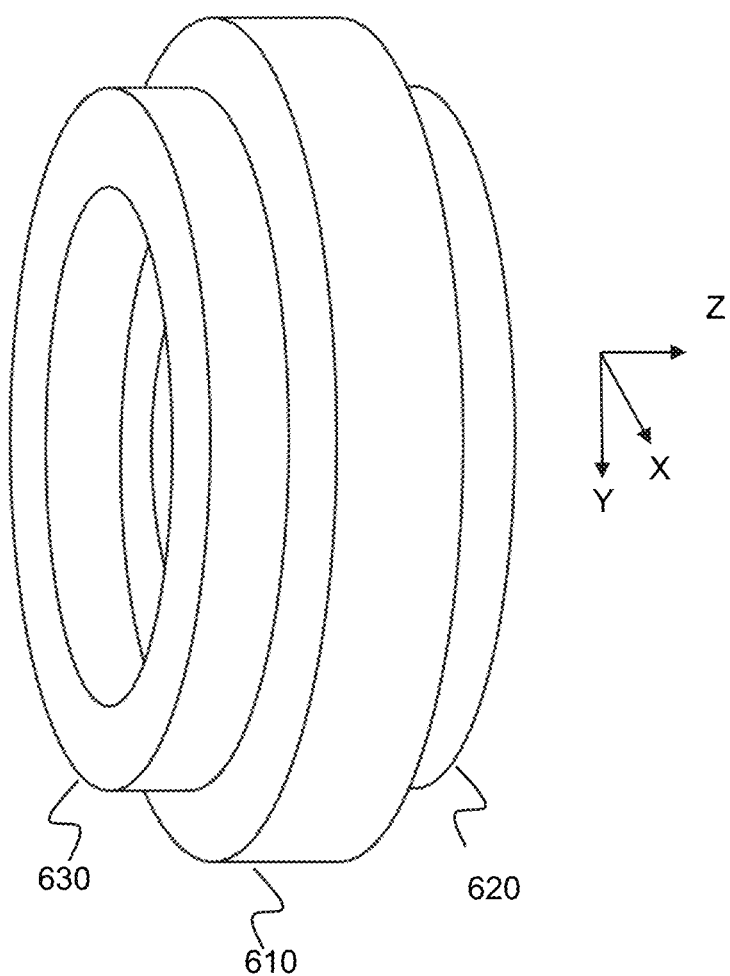
FIG. 6 is a schematic diagram illustrating a portion of an exemplary image-guided treatment apparatus according to some embodiments of the present disclosure.

FIG. 6 is a schematic diagram illustrating a portion of an exemplary image-guided treatment apparatus 110 according to some embodiments of the present disclosure. The image-guided treatment apparatus 110 may include a first ring assembly 610, a second ring assembly 620, and a third ring assembly 630. The first ring assembly 610, the second ring assembly 620, and/or the third ring assembly 630, or a portion thereof, may be made of one or more materials including for example, steel, aluminum, or any suitable alloy.

As shown in FIG. 6, the second ring assembly 620 may be located on a first side of the first ring assembly 610, and the third ring assembly 630 may be located on a second side of the first ring assembly 610. In some embodiments, the location of the second ring assembly 620 and the location of the third ring assembly 630 can be interchangeable. In some embodiments, the diameter of the first ring assembly 610 may be larger than that of the second ring assembly 620 and/or the third ring assembly 630. In some embodiments, the diameter of the second ring assembly 620 and the third ring assembly 630 may be the same. In some embodiments, the diameter of the second ring assembly 620 and the third ring assembly 630 may be different. In some embodiments, the first ring assembly 610 may include a first bore, the second ring assembly 620 may include a second bore, and the third ring assembly 630 may include a third bore. In some embodiments, the first bore, the second bore, and the third bore may share a concentric axis. In some embodiments, the first bore, the second bore, and/or the third bore may be configured to receive an object (e.g., a patient) to be subjected to radiation (e.g., radiation of treatment beams, radiation of imaging beams) in the radiation system 100. In some embodiments, the image-guided treatment apparatus 110 may include a gantry assembly (not shown) configured to support the first ring assembly 610, the second ring assembly 620, and/or the third ring assembly 630. In some embodiments, the first ring assembly 610, the second ring assembly 620, and/or the third ring assembly 630 may be placed side by side. In some embodiments, a portion of the first ring assembly 610, a portion of the second ring assembly 620, and/or a portion of the third ring assembly 630 may be operatively connected. In some embodiments, the operative connection between the first ring assembly 610, the second ring assembly 620, and/or the third ring assembly 630 may be realized by way of overlapping, mortise, occlusion, engagement, or the like.

In some embodiments, the first ring assembly 610, the second ring assembly 620, and the third ring assembly 630 may be rotatable. In some embodiments, the rotation of the first ring assembly 610 or the first radiation source may be independent of the second ring assembly 620 and/or the third ring assembly 630. In some embodiments, the rotation of the first ring assembly 610 and/or the first radiation source may be actuated mechanically, magnetically, and/or electronically. In some embodiments, the rotation of the second ring assembly 620 or the second radiation source may be independent of the first ring assembly 610 and/or the third ring assembly 630. In some embodiments, the rotation of the third ring assembly 630 or the first radiation detector may be independent of the first ring assembly 610 and/or the second ring assembly 620. In some embodiments, the first ring assembly 610, the second ring assembly 620 (or the second radiation source), and/or the third ring assembly 630 (or the first radiation detector) may rotate synchronously. For example, the rotation of the second ring assembly 620 (or the second radiation source) and the third ring assembly 630 (or the first radiation detector) may be synchronized mechanically, magnetically, and/or electronically.

In some embodiments, the first ring assembly 610 may include a first radiation source (e.g., the first radiation source of the treatment assembly 402). The first radiation source may be configured to deliver a treatment beam (e.g., X-ray beam) to a target portion of an object. In some embodiments, the treatment beam may cover a treatment region of the radiation system 100. In some embodiments, the treatment region may be located at the center of the first ring assembly 610. In some embodiments, the treatment region may be located at any position in a bore of the radiation system 100. The first radiation source may be mounted on an inner side of the first ring assembly 610. In some embodiments, the first radiation source may be moveable along the inner side of the first ring assembly 610. For example, the first radiation source may be rotatably and/or translationally moveable. In some embodiments, the rotation and/or the translation of the first radiation source may be actuated mechanically, magnetically, and/or electronically.

The second ring assembly 620 may include a second radiation source (e.g., the radiation source 461). The second radiation source may be configured to deliver a first imaging beam (e.g., X-ray beam). In some embodiments, the first imaging beam may cover a first imaging region of the radiation system. In some embodiments, the second radiation source may deliver the first imaging beam when the first radiation source delivers the treatment beam. That is, the treatment beam and the first imaging beam may be delivered simultaneously. In some embodiments, the delivery of the first imaging beam and the delivery of the treatment beam may alternate.

The third ring assembly 630 may include a first radiation detector (e.g., the radiation detector 462). The first radiation detector may be configured to detect at least a portion of the first imaging beam. In some embodiments, the first radiation detector may be a flat panel detector or a computed tomography detector. The shape of the first radiation detector may be flat, arc-shaped, circular, or the like, or any combination thereof. Merely by way of example, the first radiation detector may be a CT detector configured to detect X-ray beams. In some embodiments, the second radiation source and the first radiation detector may form an imaging assembly having a first imaging region of the radiation system 100. In some embodiments, the imaging assembly formed by the second radiation source and the first radiation detector may have an isocenter. As used herein, the isocenter of the imaging assembly may be defined as the axis of rotation of an imaging or therapy system, at the point where it intersects the plane of rotation of the imaging or therapy system. In some embodiments, if the radiation source and radiation detector of an imaging assembly are located on separate rings, the isocenter may be located on the intersection of the diagonal beam path from the radiation source to the radiation detector and a plane situated between the radiation source and the radiation detector. In some embodiments, the imaging isocenter may coincide with the treatment isocenter (e.g., the treatment isocenter of the first ring assembly 610). In some embodiments, the treatment beam may pass through the isocenter of the imaging assembly formed by the second radiation source and the first radiation detector.

In some embodiments, the second radiation source may be mounted on an inner side of the second ring assembly 620. The second radiation source may be moveable along the inner side of the second ring assembly 620. For example, the second radiation source may be rotatably and/or translationally moveable. In some embodiments, the second radiation source may be rotatable along the concentric axis of the first ring assembly 610, second ring assembly 620, and/or the third ring assembly 630. In some embodiments, the second radiation source may be rotatable along a rotation axis of its own. In some embodiments, the rotation and/or the translation of the second radiation source may be actuated mechanically, magnetically, and/or electronically. In some embodiments, the first radiation detector may be mounted on an inner side of the third ring assembly 630. The first radiation detector may be moveable along the inner side of the third ring assembly 630. For example, the first radiation detector may be rotatable and/or translationally moveable. In some embodiments, the first radiation detector may be rotatable along the concentric axis of the first ring assembly 610, second ring assembly 620, and/or the third ring assembly 630. In some embodiments, the first radiation detector may be rotatable along a rotation axis of its own. In some embodiments, the rotation and/or the translation of the first radiation detector may be actuated mechanically, magnetically, and/or electronically. In some embodiments, the first imaging beam may include diagnostic X-rays, and the second radiation source may include a diagnostic X-ray tube. In some embodiments, the diagnostic X-ray tube may direct the diagnostic X-rays in a substantially diagonal direction (e.g., with respect to the treatment beam) towards the first radiation detector in the third ring assembly 630. In some embodiments, the first ring assembly 610, the second radiation source (or the second ring assembly 620), and the first radiation detector (or the third ring assembly 630) may be positioned such that the treatment region and the first imaging region may at least partially overlap. In some embodiments, the first ring assembly 610, the second radiation source (or the second ring assembly 620), and the first radiation detector (or the third ring assembly 630) may be positioned such that the treatment region is addressable for the radiation system 100.

In some embodiments, the processing module 506 may reconstruct an image based on imaging data generated based on at least a portion of the first imaging beam detected by the first radiation detector. In some embodiments, the processing module 506 may reconstruct the image when the treatment assembly 402 (e.g., the first radiation source in the first ring assembly 610) delivers the treatment beam toward a target portion of the object. In some embodiments, the processing module 506 may generate projection data based on the at least a portion of the first imaging beam detected by the first radiation detector. The movement and/or change of the target portion of the object may be detected based on the reconstructed image, or alternatively by analyzing the projection data (e.g., comparing the projection data with reference projection data to infer the position/trajectory of an anatomical/functional region-of-interest). In some embodiments, the reference projection data may refer to imaging data generated at different times with the projection data to be analyzed. In some embodiments, the processing module 506 may determine, based on the movement and/or change of the target portion, an adjustment to the treatment plan, according to which the first radiation source may deliver an adjusted treatment beam. For example, the direction of the treatment beam may be adjusted. As another example, the position and/or direction (e.g., a tilting angle) of the first radiation source may be adjusted. In some embodiments, the processing module 506 may determine that the position of the object needs to be adjusted with respect to the treatment beam by way of adjusting, e.g., the table 114 on which the object is supported during the treatment.

In some embodiments, the radiation system 100 may include a first position sensor and a second position sensor (not shown). For instance, the first position sensor and/or the second position sensor may be angular position sensors. The first position sensor may be configured to record a motion of the second ring assembly 620. The second position sensor may be configured to record a motion of the third ring assembly 630. The motion of the second ring assembly 620 and/or the third ring assembly 630 may include rotation, translation, etc. In some embodiments, the motion of the second ring assembly 620 and/or the third ring assembly 630 may be actuated mechanically, magnetically, and/or electronically. The processing module 506 may determine a motion difference between the second ring assembly 620 and the third ring assembly 630 based on the recorded motion of the second ring assembly 620 and the recorded motion of the third ring assembly 630. The motion difference may include a rotational phase difference (e.g., 5, 10, 15 degrees) between the rotation of the second ring assembly 620 and the rotation of the third ring assembly 630. The motion difference may also include a translational difference between the translation of the second ring assembly 620 and the translation of the third ring assembly 630. In some embodiments, the translation of the second ring assembly 620 and/or the translation of the third ring assembly 630 may occur due to, e.g., an eccentric force generated by the rotation movement. For instance, the second ring assembly 620 may move a first distance along a direction of the concentric axis of the first ring assembly 610, second ring assembly 620, and/or the third ring assembly 630. The third ring assembly 630 may move a second distance along the direction of the concentric axis. The translational difference may be a difference between the first distance and the second distance. When reconstructing the image, the processing module 506 may take into consideration the difference between the second ring assembly 620 and the third ring assembly 630. The processing module 506 may process the imaging data by compensating the difference. Merely by way of example, the motion difference between the second ring assembly 620 and the third ring assembly 630 may include a rotational phase difference and a translation difference which is negligible. The processing module 506 may process the imaging data by compensating for, or simply accounting for, the rotational phase difference. In some embodiments, the processing module 506 may then reconstruct the image based on the processed imaging data. In some embodiments, the processing module 506 may determine whether there is a motion of an object based on the processed imaging data.

In some embodiments, the image-guided treatment apparatus 110 may be configured to include more than one imaging regions. For instance, the image-guided treatment apparatus 110 may be configured to include at least one first imaging region that at least partially overlaps with the treatment region of the image-guided treatment apparatus 110 and at least one second imaging region the imaging beam of which passes through the isocenter of the imaging assembly generating the imaging beam. In some embodiments, the first imaging region and the second imaging region may be different or partially different. In some embodiments, a first isocenter of a first imaging assembly including the first imaging region and a second isocenter of a second imaging assembly including the second imaging region may be different. An imaging region that at least partially overlaps with the treatment region may be formed by a radiation source and a radiation detector located diagonally on different sides of the first ring assembly 610, e.g., the second radiation source in the second ring assembly 620 and the first radiation detector in the third ring assembly 630. In some embodiments, the image-guided treatment apparatus 110 may be configured to include more than one imaging region that at least partially overlap with the treatment region of the image-guided treatment apparatus 110. An imaging region the imaging beam of which passes through the isocenter of the imaging assembly generating the imaging beam may be formed by a radiation source and a radiation detector located on the same side of the first ring assembly 610, e.g., the second radiation source and a radiation detector both located in the second ring assembly 620. It should be noted that in some embodiments, the treatment region may be addressable for the radiation system 100 even if the treatment region does not overlap with the imaging region. In some embodiments, a reference portion of an object associated with a target portion of the object may be located in the imaging region(s) of the image-guided treatment apparatus 110, and the position of the target portion may be determined based on the position of the reference portion. The reference portion may be a surrogate region (e.g., a diaphragm), so that the target portion (e.g., a lung, a liver, a stomach, etc.) may be addressed and located in the treatment region of the radiation system 100.

In some embodiments, the second ring assembly 620 may also include a second radiation detector. The second radiation detector may be configured to detect an imaging beam. In some embodiments, the second radiation detector may be a flat panel detector or a computed tomography detector. The shape of the second radiation detector may be flat, arc-shaped, circular, or the like, or any combination thereof. Merely by way of example, the second radiation detector may be a CT detector configured to detect X-ray beams. In some embodiments, the second radiation source in the second ring assembly 620 may coordinate with the first radiation detector in the third ring assembly 630 forming an imaging assembly. In some embodiments, the second radiation source in the second ring assembly 620 may coordinate with the second radiation detector in the second ring assembly 620 forming a different imaging assembly.

In some embodiments, the second radiation source may be movable between a first position and a second position. The second radiation source at the first position may deliver the first imaging beam towards the first radiation detector in the third ring assembly 630. The second radiation source at the second position may deliver a second imaging beam (e.g., X-ray beam) toward the second radiation detector in the second ring assembly 620. In some embodiments, the second radiation source at the second position and the second radiation detector may form an imaging assembly having an isocenter. As used herein, the isocenter of the imaging assembly may be located on the axis of rotation of an imaging or therapy system (e.g., the imaging assembly formed by the second radiation source at the second position and the second radiation detector). In some embodiments, if the radiation source and radiation detector of an imaging assembly are located on separate rings, the isocenter may be located on a diagonal beam path from the radiation source to the radiation detector. In some embodiments, the first imaging beam from the second radiation source to the first radiation detector may pass through the treatment isocenter (e.g., the treatment isocenter of the first ring assembly 610), and moreover the imaging isocenter may substantially coincide with the treatment isocenter. The second imaging beam may not pass through the treatment isocenter while indeed passing through the imaging isocenter defined by the second radiation source and the second detector. In some embodiments, the motion of the second radiation source between the first position and the second position may include a translation and/or a rotation (e.g., a tilt between the first position and the second position). In some embodiments, the motion of the second radiation source may be actuated mechanically, magnetically, and/or electronically.

In some embodiments, the second ring assembly 620 may also include a third radiation source configured to deliver a third imaging beam. In some embodiments, the third radiation source and the second radiation source may be positioned side by side. In some embodiments, the third radiation source and the second radiation source may be positioned side by side along an axial direction of the second ring assembly 620. In some embodiments, the third radiation source and the second radiation source may be positioned side by side along a peripheral direction of the second ring assembly 620. In some embodiments, the first imaging beam, the second imaging beam, and/or the third imaging beam may have the same energy. In some embodiments, the first imaging beam, the second imaging beam, and/or the third imaging beam may have different energies. For example, the second radiation source and the third radiation source may include diagnostic X-ray tubes. The tube voltages of the diagnostic X-ray tubes of the second radiation source and the third radiation source may be substantially same or substantially different.

In some embodiments, in the second ring assembly 620, the third radiation source and the second radiation detector may form an imaging assembly, and thus the third radiation source may deliver the third imaging beam toward the second radiation detector. Moreover, an isocenter could be located between the third radiation source and the second radiation detector, through which the third imaging beam from the third radiation source to the second radiation detector may pass. In some embodiments, the third imaging beam may cover a second imaging region of the image-guided treatment apparatus 110. In some embodiments, the second imaging region may be different form the first imaging region. For example, the second imaging region may be formed by a radiation source and a radiation detector located in the same ring assembly (e.g., both located in the second ring assembly 620), while the first imaging region may be formed by a radiation source and a radiation detector located in different ring assembly (e.g., in the second ring assembly 620 and the third ring assembly 630, respectively).

In some embodiments, the second ring assembly 620 may also include a third radiation detector. The third radiation detector may be configured to detect at least a portion of the third imaging beam delivered from the third radiation source. In some embodiments, the third radiation detector may be a flat panel detector or a computed tomography detector. The shape of the third radiation detector may be flat, arc-shaped, circular, or the like, or any combination thereof. In some embodiments, the third radiation source and the third radiation detector may form an imaging assembly having an isocenter. In some embodiments, the third imaging beam may pass through the isocenter defined by the third radiation source and third radiation detector. In some embodiments, the third radiation detector and the second radiation detector may be positioned side by side. In some embodiments, the third radiation source in the second ring assembly 620 may deliver the third imaging beam, covering a third imaging region, toward the first radiation detector in the third ring assembly 630. The third imaging region may at least partially overlap with the first imaging region. Moreover, the third imaging region may at least partially overlap with the treatment region of the radiation system 100.

In some embodiments, the third ring assembly 630 may also include a fourth radiation source configured to deliver a fourth imaging beam to the second radiation detector and/or a fifth imaging beam to the third radiation detector. The second radiation detector (and/or the third radiation detector) in the second ring assembly 620 may detect at least a portion of the fourth imaging beam (and/or the fifth imaging beam). The fourth radiation source in the third ring assembly 630 and the second radiation detector (and/or the third radiation detector) in the second ring assembly 620 may define a fourth imaging region of the imaging system 100. In some embodiments, the fourth imaging beam and/or the fifth imaging beam may cover the fourth imaging region. In some embodiments, the fourth imaging beam and/or the fifth imaging beam may include diagnostic X-rays, and the fourth radiation source may include a diagnostic X-ray tube. In some embodiments, the fourth imaging beam and the fifth imaging beam may have the same energy. In some embodiments, the fourth imaging beam and the fifth imaging beam may have different energies. The diagnostic X-ray tube may direct the diagnostic X-rays in a substantially diagonal direction (e.g., with respect to the treatment beam) toward the second radiation detector (and/or the third radiation detector) in the second ring assembly 620. In some embodiments, the fourth imaging region and the first imaging region may overlap at an overlapping region. In some embodiments, the overlapping region may be substantially inside the bore of the first ring assembly 610. In some embodiments, the fourth imaging region and the treatment region may at least partially. Moreover, the overlapping region and the treatment region may at least partially overlap. In some embodiments, the third ring assembly 630 further includes a fourth radiation detector configured to detect at least a portion of the imaging beam from the fourth radiation source.

It should be noted that the second ring assembly 620 may include one or more radiation sources and one or more radiation detectors, and the third ring assembly 630 may include one or more radiation sources and one or more radiation detectors. In some embodiments, one radiation source of the second ring assembly 620 and one radiation detector of the second ring assembly 620 may form an imaging assembly. In some embodiments, one radiation source of the second ring assembly 620 and one radiation detector of the third ring assembly 630 may form an imaging assembly. In some embodiments, one radiation source of the third ring assembly 630 and one radiation detector of the third ring assembly 630 may form an imaging assembly. In some embodiments, one radiation source of the third ring assembly 630 and one radiation detector of the second ring assembly 620 may form an imaging assembly. In some embodiments, a same radiation source of the second ring assembly 620, if located at a first position, may form an imaging assembly with one radiation detector of the second ring assembly 620, and if located at a second position, may form an imaging assembly with one radiation detector of the third ring assembly 630. In some embodiments, a same radiation source of the third ring assembly 630, if located at a first position, may form an imaging assembly with one radiation detector of the third ring assembly 630, and if located at a second position, may form an imaging assembly with one radiation detector of the second ring assembly 620.

In some embodiments, the first radiation source of the first ring assembly 610 may be used as an imaging source (e.g., a CBCT source), and the first radiation source may deliver an imaging beam (e.g., a cone beam). In some embodiments, the second radiation detector and/or the third radiation detector of the second ring assembly 620 may detect at least a portion of the imaging beam delivered from the first radiation source of the first ring assembly 610. In some embodiments, the first radiation detector and/or the fourth radiation detector of the third ring assembly 630 may detect at least a portion of the imaging beam delivered by the first radiation source of the first ring assembly 610. For example, the first radiation source may be movable between a third position, a fourth position, and a fifth position. In some embodiments, the first radiation source at the third position may deliver the treatment beam toward an object or an imaging beam toward a radiation detector opposite to the first radiation source. In some embodiments, the first radiation source at the fourth position may deliver the treatment beam toward the object or an imaging beam (e.g., X-ray beam) toward the second radiation detector and/or the third radiation detector in the second ring assembly 620. In some embodiments, the first radiation source at the fifth position may deliver the treatment beam toward the object or an imaging beam (e.g., X-ray beam) toward the first radiation detector and/or the fourth radiation detector of the third ring assembly 630. In some embodiments, the first radiation source at the fourth position and the second radiation detector or the third radiation detector may form an imaging assembly having an isocenter. In some embodiments, the first radiation source at the fifth position and the first radiation detector or the fourth radiation detector may form an imaging assembly having an isocenter. In some embodiments, the motion of the first radiation source between the third position, the fourth position, and the fifth position may include a translation and/or a rotation (e.g., a tilt between the third position and the fourth (or fifth) position). In some embodiments, the motion of the first radiation source may be actuated mechanically, magnetically, and/or electronically.

In some embodiments, the first ring assembly 610 may further include a fifth radiation detector. The fifth radiation detector may detect at least a portion of the imaging beam delivered from the first radiation source of the first ring assembly 610, at least a portion of the imaging beam delivered from the second radiation source and/or the third radiation source of the second ring assembly 620, and/or at least a portion of the imaging beam delivered from the fourth radiation source of the third ring assembly 630.

In some embodiments, the first ring assembly 610 may include one or more radiation sources and one or more radiation detectors. In some embodiments, one radiation detector of the first ring assembly 610 may detect at least a portion of the imaging beam delivered from one radiation source of the first ring assembly 610, the second ring assembly 620, and/or the third ring assembly 630. In some embodiments, one radiation detector of the second ring assembly 620 and/or the third ring assembly 630 may detect at least a portion of the imaging beam delivered from one radiation source of the first ring assembly 610.

In some embodiments, a ring assembly (e.g., first ring assembly 610, the second ring assembly 620, and/or the third ring assembly 630) may include one or more radiation sources and/or one or more radiation detectors. In some embodiments, a ring assembly may include one or more support structures. In some embodiments, the radiation source(s), the radiation detector(s), and/or the support structure(s) may be assembled so that a trajectory of the rotation of the radiation source(s) and/or the radiation detector(s) may be a ring shape. In some embodiments, the radiation source(s) and/or the radiation detector(s) may rotate while the support structure stays still. In some embodiments, the radiation source(s) and/or the radiation detector(s), may rotate with the support structure(s).

It should be understood that the teachings contained herein relating to the rotation, translation, tilting, or other motion of a radiation source apply also to radiation sources that are moved by means other than mechanical actuation. For example, a radiation beam (also referred to as an imaging beam) may be scanned electronically or magnetically, such as is the case in electron beam CT, scanning-mode particle therapy, etc.

It should be noted that the above description of the image-guided treatment apparatus 110 is merely provided for the purposes of illustration, and not intended to limit the scope of the present disclosure. For persons having ordinary skills in the art, multiple variations or modifications may be made under the teachings of the present disclosure. For example, the image-guided treatment apparatus 110 in FIG. 6 may further include one or more components, such as one or more connecting pieces to connect the first ring assembly 610, the second ring assembly 620, and/or the third ring assembly 630. As another example, the number of the radiation sources and/or the radiation detectors mounted on the second ring assembly 620 and/or the third ring assembly 630 is not limiting.

Figure 7:
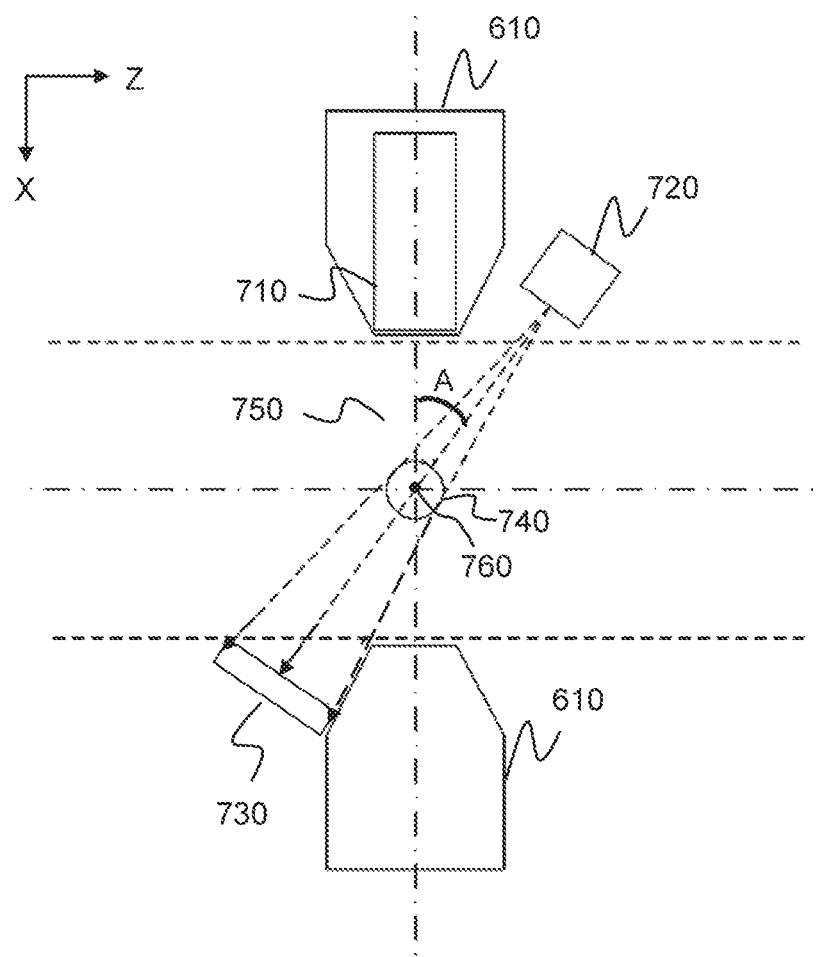
FIG. 7 is a schematic diagram illustrating the section view in an X-Z plane of an exemplary image-guided treatment apparatus according to some embodiments of the present disclosure.

FIG. 7 is a schematic diagram illustrating the section view in an X-Z plane of an exemplary image-guided treatment apparatus 110 according to some embodiments of the present disclosure. In the present disclosure, the X axis direction may be from the right side to the left side of the image-guided treatment apparatus 110, as shown in FIGS. 1 and 6-8. The Y axis direction may be from the upper part to the lower part of the image-guided treatment apparatus 110, as shown in FIGS. 1 and 6-8. The Z axis direction may be from the front to the rear of the image-guided treatment apparatus 110 along the axis of the bore, as shown in FIGS. 1 and 6-8.

As shown in FIG. 7, the image-guided treatment apparatus 110 may include a first radiation source 710, a second radiation source 720, and a first radiation detector 730. In some embodiments, the first radiation source 710 may be rotatably mounted on a first ring assembly 610. In some embodiments, the first ring assembly 610, the second radiation source 720, and/or the first radiation detector 730 may be supported by a gantry assembly (not shown in FIG. 7). The first radiation source 710 may be configured to deliver a treatment beam to an object (e.g., a patient) received by a bore 750 of the first ring assembly 610. The first ring assembly 610 may have a treatment region where the object receives treatment. The treatment region may be located in the center region of the first ring assembly 610 or the bore of the first ring assembly 610. The second radiation source 720 and the first radiation detector 730 may be respectively positioned on two different sides of the first ring assembly 610. The second radiation source 720 may deliver an imaging beam (e.g., X-ray beam) to the object in a substantially diagonal direction (e.g., with respect to the treatment beam) toward the first radiation detector 730. The first radiation detector 730 may be configured to detect at least a portion of the imaging beam. The second radiation source 720 and the first radiation detector 730 may form an imaging assembly having a first imaging region. The first ring assembly 610 (or the first radiation source 710), the second radiation source 720, and the first radiation detector 730 may be positioned such that the first imaging region and the treatment region may at least partially overlap (e.g., at an overlapping region 740). In some embodiments, the first radiation detector 730 may partially extend into the bore 750 of the first ring assembly 610. In some embodiments, the second radiation source 720 may be rotatably mounted on a second ring assembly (e.g., the second ring assembly 620 shown in FIG. 6). In some embodiments, the first radiation detector 730 may be rotatably mounted on a third ring assembly (e.g., the third ring assembly 630 shown in FIG. 6).

The first ring assembly 610, the second ring assembly, and/or the third ring assembly may be rotatable. In some embodiments, the rotation of the first ring assembly 610 may be independent of the second ring assembly and/or the third ring assembly. In some embodiments, the rotation of first ring assembly 610 may be actuated mechanically, magnetically, and/or electronically. In some embodiments, the rotation of the second ring assembly may be independent of the first ring assembly 610 and/or the third ring assembly. In some embodiments, the rotation of the third ring assembly may be independent of the first ring assembly 610 and/or the second ring assembly. In some embodiments, the second ring assembly and the third ring assembly may rotate synchronously. In some embodiments, the rotation of the second ring assembly and the rotation of the third ring assembly may be synchronized mechanically, magnetically, and/or electronically. For instance, the second ring assembly and the third ring assembly may be mechanically connected together so that they rotate synchronously.

In some embodiments, a center line of the first imaging beam delivered by the second radiation source 720 and a center line of the treatment beam delivered by the first radiation source 710 may intersect at an isocenter 760 of the image-guided treatment apparatus 110.

In some embodiments, the imaging assembly may have an axis. In some embodiments, the treatment assembly may have an axis. In some embodiments, the axis of the imaging assembly or the treatment assembly may be defined by the pathway of a central ray of the imaging beam generated by the imaging assembly or the treatment beam generated by the treatment assembly (also referred to as the treatment system central axis [CAX]). In some embodiments, the axis of the imaging assembly may be defined by a line connecting the center or focus of the radiation source and the center of the radiation detector. In some embodiments, the axis of the treatment assembly may co-incide with a line along the central axis of the treatment beam. The axis of the imaging assembly may be at an angle A with the axis of the treatment assembly. In some embodiments, the angle may be no more than 60°, or no more than 50°, or no more than 45°, or no more than 40°, or no more than 35°, or no more than 30°. Merely by way of example, the angle is 30° or less. In some embodiments, the radiation source and/or the radiation detector may partially extend into the bore of the first ring assembly 610. For instance, as illustrated in FIG. 7, the angle A may be the angle between a center line of the first imaging beam delivered by the second radiation source 720 and a center line of the treatment beam delivered by the first radiation source 710. In some embodiments, as compared with relatively large angle, with relatively small angle A, the imaging quality of the target portion of the object may be better. In some embodiments, the first radiation detector in the third ring assembly 630 may partially extend into the first bore of the first ring assembly 610 in order to reduce the angle A, so that the imaging quality may be improved. That is, the mounting angle of the first radiation detector 730 could be adjustable.

In some embodiments, the first radiation source 710 may be used as an imaging source (e.g., a CBCT source that could be the treatment source per se, or a CBCT source, some components and/or parameters of which (for example, the target impinged by electrons) are different from the treatment source but are housed within a same treatment head), and the first radiation source 710 may deliver an imaging beam (e.g., a cone beam). In some embodiments, the first radiation detector 730 may detect at least a portion of the imaging beam delivered by the first radiation source 710. In some embodiments, the first ring assembly 610 may further include a fifth radiation detector, e.g., a detector of an electronic portal imaging device (EPID). The fifth radiation detector may detect at least a portion of the imaging beam delivered from the first radiation source 710, and/or at least a portion of the imaging beam delivered from the second radiation source 720. For example, the first radiation source may be movable between a third position, a fourth position, and a fifth position. In some embodiments, the first radiation source at the third position may deliver the treatment beam toward an object or an imaging beam toward a radiation detector opposite to the first radiation source. In some embodiments, the first radiation source at the fourth position may deliver the treatment beam toward the object or an imaging beam (e.g., X-ray beam) toward the second radiation detector and/or the third radiation detector in the second ring assembly 620. In some embodiments, the first radiation source at the fifth position may deliver the treatment beam toward the object or an imaging beam (e.g., X-ray beam) toward the first radiation detector and/or the fourth radiation detector of the third ring assembly 630. In some embodiments, the first radiation source at the fourth position and the second radiation detector or the third radiation detector may form an imaging assembly having an isocenter. In some embodiments, the first radiation source at the fifth position and the first radiation detector or the fourth radiation detector may form an imaging assembly having an isocenter. In some embodiments, the motion of the first radiation source between the third position, the fourth position, and the fifth position may include a translation and/or a rotation (e.g., a tilt between the third position and the fourth (or fifth) position). In some embodiments, the motion of the first radiation source may be actuated mechanically, magnetically, and/or electronically.

Figure 8:
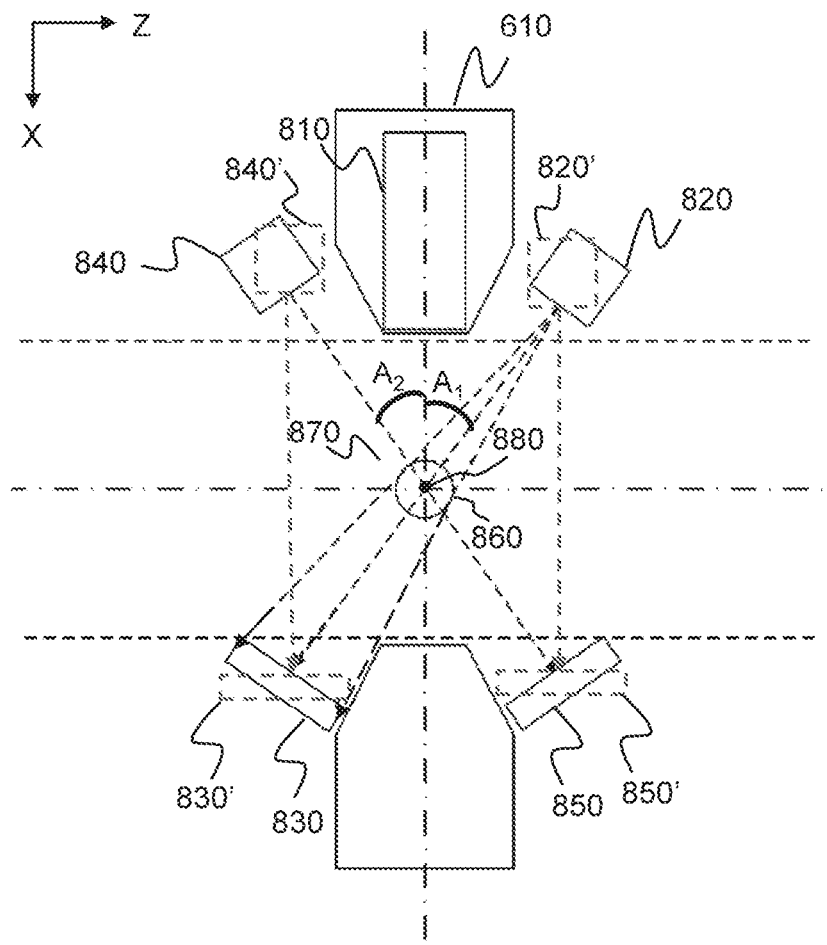
FIG. 8 is a schematic diagram illustrating the section view in an X-Z plane of an exemplary image-guided treatment apparatus according to some embodiments of the present disclosure.

FIG. 8 is a schematic diagram illustrating the section view in an X-Z plane of an exemplary image-guided treatment apparatus 110 according to some embodiments of the present disclosure. As shown in FIG. 8, the image-guided treatment apparatus 110 may include a first ring assembly 610, a first radiation source 810, a second radiation source 820, a first radiation detector 830, a fourth radiation source 840, and a second radiation detector 850. The first ring assembly 610, the first radiation source 810, the second radiation source 820, the first radiation detector 830, the fourth radiation source 840, and/or the second radiation detector 850 may be supported by a gantry assembly (not shown in FIG. 8). In some embodiments, the first radiation source 810 may be rotatably mounted on the first ring assembly 610.

The first radiation source 810 may be configured to deliver a treatment beam to an object (e.g., a patient) received by a bore 870 of the first ring assembly 610. The first ring assembly 610 may have a treatment region relating to the object. The treatment region may be located in the center of the first ring assembly 610. The second radiation source 820 and the first radiation detector 830 may be respectively positioned on two different sides of the first ring assembly 610. The second radiation source 820 may deliver a first imaging beam (e.g., X-ray beam) to the object in a substantially diagonal direction (e.g., with respect to the treatment beam) toward the first radiation detector 830. The first radiation detector 830 may be configured to detect at least a portion of the first imaging beam. The second radiation source 820 and the first radiation detector 830 may form an imaging assembly having a first imaging region. The fourth radiation source 840 and the second radiation detector 850 may be respectively positioned on two different sides of the first ring assembly 610. The fourth radiation source 840 may deliver a fourth imaging beam (e.g., X-ray beam) to the object in a substantially diagonal direction (e.g., with respect to the treatment beam) toward the second radiation detector 850. The second radiation detector 850 may be configured to detect at least a portion of the fourth imaging beam. The fourth radiation source 840 and the second radiation detector 850 may form an imaging assembly having a fourth imaging region (not shown). In some embodiments, the fourth imaging region and the first imaging region may overlap at an overlapping region 860. In some embodiments, the overlapping region 860 and the treatment region may at least partially overlap.

In some embodiments, the first imaging beam and the fourth imaging beam may have different energies. In some embodiments, a center line of the first imaging beam delivered by the second radiation source 820, a center line of the treatment beam delivered by the first radiation source 810, and/or a center line of the fourth imaging beam (and/or the fifth imaging beam) delivered by the fourth radiation source 840 may intersect at an isocenter 880 of the image-guided treatment apparatus 110. In some embodiments, a center line of the first imaging beam delivered by the second radiation source 820 and a center line of the treatment beam delivered by the first radiation source 810 may form a first angle $A_1$. In some embodiments, a center line of the treatment beam delivered by the first radiation source 810 and a center line of the fourth imaging beam (and/or the fifth imaging beam) delivered by the fourth radiation source 840 may form a second angle $A_2$. In some embodiments, the first angle $A_1$ and the second angle $A_2$ may be the same or different. In some embodiments, the first radiation detector 830 may partially extend into the first bore of the first ring assembly 610 in order to reduce the first angle $A_1$, so that the imaging quality may be improved. In some embodiments, the second radiation detector 850 may partially extend into the first bore of the first ring assembly 610 in order to reduce the second angle $A_2$, so that the imaging quality may be improved. That is, the mounting angle of the first radiation detector 830 and the second radiation detector 850 could be adjustable. In some embodiments, the signals detected by the first radiation detector 830 and the second radiation detector 850 may be combined for reconstructing a single image with improved quality.

In some embodiments, the second radiation source 820 or another radiation source (not shown) may form a first imaging assembly with the second radiation detector 850 or another radiation detector (not shown), in one state as illustrated by 820' and 850' using the dashed lines in FIG. 8. In some embodiments, the fourth radiation source 840 or another radiation source (not shown) may form a second imaging assembly with the first radiation detector 830 or another radiation detector (not shown), in one state as illustrated by 840' and 830' using the dashed lines in FIG. 8. In some embodiments, the image generated based on the first imaging beam and/or the fourth imaging beam may have one or more artifacts, and then one or more images generated by the first imaging assembly and/or the second imaging assembly may help to reduce the artifacts and thereby improve image quality.

It should be noted that in some embodiments, the second radiation source 820 and the second radiation detector 850 may be rotatably mounted on a second ring assembly (e.g., the second ring assembly 620 shown in FIG. 6). In some embodiments, the fourth radiation source 840 and the first radiation detector 830 may be rotatably mounted on a third ring assembly (e.g., the third ring assembly 630 shown in FIG. 6).

In some embodiments, the first radiation source 810 may be used as an imaging source (e.g., a CBCT source), and the first radiation source 810 may deliver an imaging beam (e.g., a cone beam). In some embodiments, the first radiation detector 830 and/or the second radiation detector 850 may detect at least a portion of the imaging beam delivered by the first radiation source 810. In some embodiments, the first ring assembly 610 may further include a fifth radiation detector. The fifth radiation detector may detect at least a portion of the imaging beam delivered from the first radiation source 810, at least a portion of the imaging beam delivered from the second radiation source 820, and/or at least a portion of the imaging beam delivered from the fourth radiation source 840. For example, the first radiation source may be movable between a third position, a fourth position, and a fifth position. In some embodiments, the first radiation source at the third position may deliver the treatment beam toward an object or an imaging beam toward a radiation detector opposite to the first radiation source. In some embodiments, the first radiation source at the fourth position may deliver the treatment beam toward the object or an imaging beam (e.g., X-ray beam) toward the second radiation detector and/or the third radiation detector in the second ring assembly 620. In some embodiments, the first radiation source at the fifth position may deliver the treatment beam toward the object or an imaging beam (e.g., X-ray beam) toward the first radiation detector and/or the fourth radiation detector of the third ring assembly 630. In some embodiments, the first radiation source at the fourth position and the second radiation detector or the third radiation detector may form an imaging assembly having an isocenter. In some embodiments, the first radiation source at the fifth position and the first radiation detector or the fourth radiation detector may form an imaging assembly having an isocenter. In some embodiments, the motion of the first radiation source between the third position, the fourth position, and the fifth position may include a translation and/or a rotation (e.g., a tilt between the third position and the fourth (or fifth) position). In some embodiments, the motion of the first radiation source may be actuated mechanically, magnetically, and/or electronically.

Figure 9:
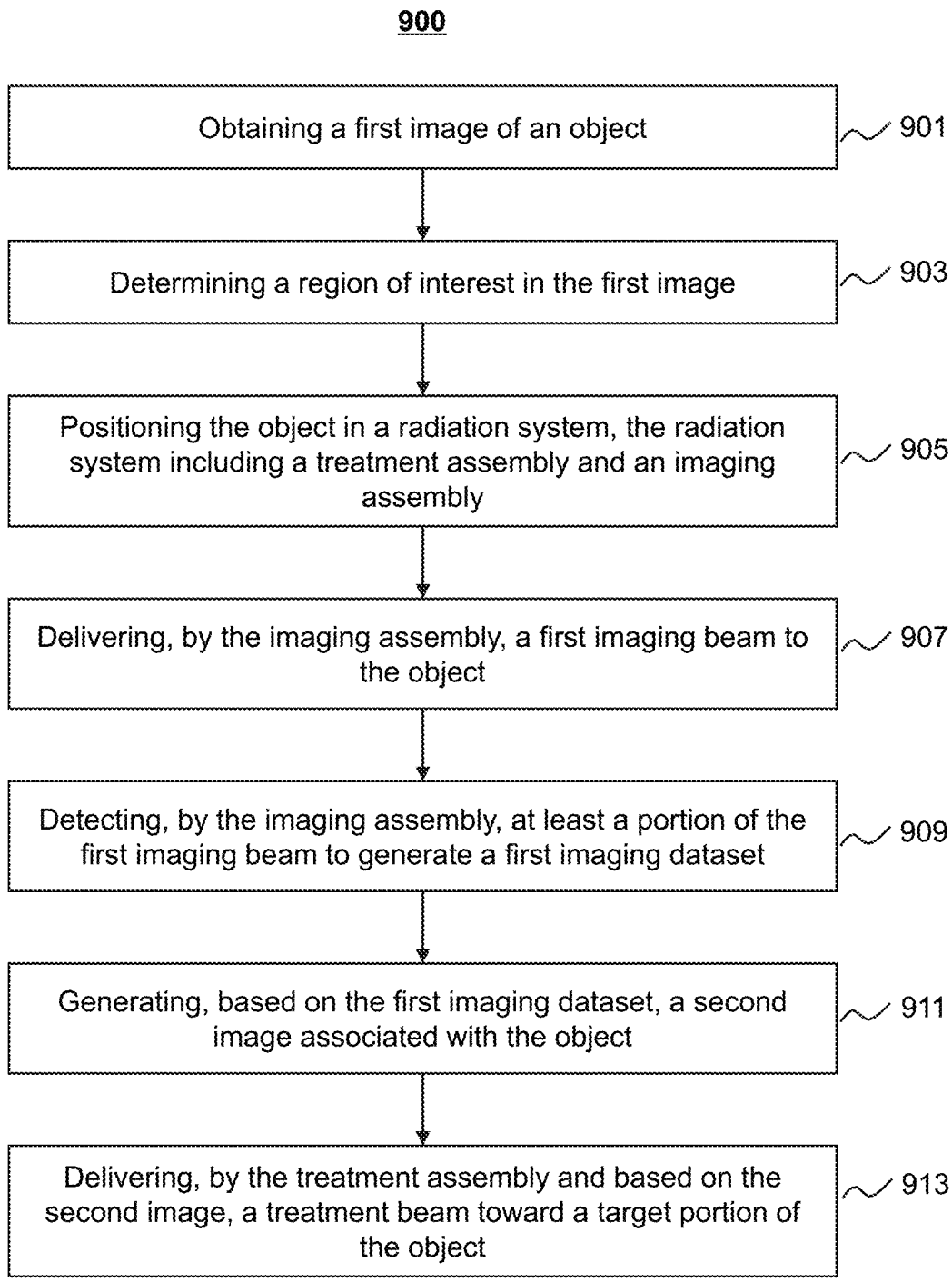
FIG. 9 is a flowchart illustrating an exemplary process for image-guided radiotherapy according to some embodiments of the present disclosure.

FIG. 9 is a flowchart illustrating an exemplary process 900 for image-guided radiotherapy according to some embodiments of the present disclosure. The process 900 may be executed by the radiation system 100. For example, the process 900 may be stored in the storage device 150 and/or the storage 220 in the form of instructions (e.g., an application), and invoked and/or executed by the processing device 150 (e.g., the processor 210 illustrated in FIG. 2, or one or more modules in the processing device 140 illustrated in FIG. 5). In some embodiments, one or more operations of the process 900 may be performed with manual intervention. The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 901, the processing device 140 (e.g., the acquisition module 502) may obtain a first image of an object. In some embodiments, the processing device 140 may obtain the first image from a storage device, for example, the storage device 150, or an external storage source (not shown). The first image may be generated using an imaging system. In some embodiments, the imaging system may be a computed tomography (CT) system. In some embodiments, the first image may be generated by an imaging assembly of the image-guided treatment apparatus 110. In some embodiments, the first image may be a two-dimensional (2D) image, a three-dimensional (3D) image, a four-dimensional (4D) image, etc. In some embodiments, the first image may be a planning image (e.g., a planning CT image) or a previously determined 3D or 4D image. The object may include a substance, a tissue, an organ, a specimen, a body, or the like, or any combination thereof. In some embodiments, the object may include a patient or a part thereof (e.g., a head, a breast, an abdomen, etc.). In some embodiments, the first image may be obtained based on one or more instructions or manipulations of an operator (e.g., a doctor). For example, the first image may be obtained based on one or more imaging parameters input or selected by the operator.

In 903, the processing device 140 (e.g., the processing module 506) may determine a region of interest (ROI) in the first image. The ROI may refer to a part of the object in the first image. In some embodiments, the ROI may be a region of cancerous and/or non-cancerous target which needs to be treated by the radiation system 100. The ROI may include a cell, a tissue, an organ (e.g., a prostate, a lung, a brain, a spine, a liver, a pancreas, a breast, etc.), or any combination thereof. In some embodiments, the ROI may be a tumor, an organ with tumor, or a tissue with tumor. In some embodiments, the processing device 140 may determine the ROI in the first image based on an image segmentation algorithm. The image segmentation algorithm may include a threshold algorithm, a region growing algorithm, an algorithm based on an energy function, a level set algorithm, a region segmentation and/or merging, an edge tracking segmentation algorithm, a statistical pattern recognition algorithm, a mean clustering segmentation algorithm, a model algorithm, a segmentation algorithm based on a deformable model, an artificial neural networks method, a minimum path segmentation algorithm, a tracking algorithm, a segmentation algorithm based on a rule, a coupling surface segmentation algorithm, or the like, or any combination thereof. In some embodiments, the ROI may be determined based on one or more instructions or manipulations of an operator (e.g., a doctor). For example, the ROI may be selected or edited by the operator.

In 905, the processing device 140 may position the object in a radiation system. The radiation system may include a treatment assembly and an imaging assembly (e.g., the radiation system 100 shown in FIG. 1). The first image may include information related to the location of the ROI. In some embodiments, the object may be positioned in a bore of the image-guided treatment apparatus 110 to receive radiation based on the information related to the location of the ROI. In some embodiments, the processing device 140 may determine a position relationship between the ROI in the first image and a treatment beam in the radiation system. In some embodiments, the processing device 140 (e.g., the control module 504) may position the object in the radiation system based on the position relationship, so that the object may be positioned in a treatment region of the radiation system. In some embodiments, the object may be positioned based on one or more instructions or manipulations of an operator (e.g., a doctor). For example, the position of the object may be adjusted by the operator before, during, and/or after the processing device 140 positions the object.

In some embodiments, the radiation system may include the image-guided treatment apparatus 110. The image-guided treatment apparatus 110 may include a treatment assembly and an imaging assembly. In some embodiments, the image-guided treatment apparatus 110 may include more than one imaging assembly. The treatment assembly may include a first radiation source in a first ring assembly (e.g., the first ring assembly 610 of the image-guided treatment apparatus 110). The imaging assembly may include a second radiation source in a second ring assembly (e.g., the second ring assembly 620 of the image-guided treatment apparatus 110). The imaging assembly may also include a first radiation detector in a third ring assembly (e.g., the third ring assembly 630 of the image-guided treatment apparatus 110). The second ring assembly may be located at a first side of the first ring assembly, and the third ring assembly may be located at a second side of the first ring assembly (as illustrated in FIGS. 6-8).

In 907, the imaging assembly (e.g., the second radiation source in the second ring assembly 620) may deliver a first imaging beam (e.g., X-ray beam) to the object. In some embodiments, the first imaging beam may be delivered based on one or more instructions or manipulations of an operator (e.g., a doctor). For example, the X-ray energy of the first imaging beam may be set by the operator.

In 909, the imaging assembly (e.g., the first radiation detector in the third ring assembly 630) may detect at least a portion of the first imaging beam to generate a first imaging dataset. In some embodiments, the first imaging dataset may include raw data such as projection data. In some embodiments, the second radiation source in the second ring assembly 620 may deliver the first imaging beam toward the first radiation detector in the third ring assembly 630 in a substantially diagonal direction (e.g., with respect to the treatment beam). The first radiation detector in the third ring assembly 630 may detect at least a portion of the first imaging beam to generate the first imaging dataset.

In 911, the processing device 140 (e.g., the processing module 506) may generate, based on the first imaging dataset, a second image associated with the object (e.g., the ROI, or a reference portion of the object). The reference portion may be a surrogate region (e.g., a diaphragm), so that a target portion (e.g., a lung, a liver, a stomach, etc.) to be treated by radiation may be addressed and located in the treatment region of the radiation system 100. In some embodiments, the processing device 140 may reconstruct the second image based on the first imaging dataset according to a reconstruction algorithm. The reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. In some embodiments, the second image may include the ROI. In some embodiments, the second image may include a surrogate region (e.g., a diaphragm) instead of the ROI. In some embodiments, the second image may be generated based on one or more instructions or manipulations of an operator (e.g., a doctor). For example, one or more reconstruction parameters may be set by the operator.

As disclosed elsewhere (e.g., FIG. 6 and the description thereof) in the present disclose, the rotation of the second ring assembly (including the second radiation source) and the third ring assembly (including the first radiation detector) may be synchronous. In some embodiments, the processing device 140 may determine that there is a motion difference (e.g., a rotational phase difference, a translational difference, or a combination thereof) between the rotation of the second ring assembly and the rotation of the third ring assembly. For instance, the rotational phase difference (e.g., 5, 10, 15 degrees) may affect the accuracy of the first imaging dataset and accordingly affect the quality of the second image. For example, the motion difference may introduce artifacts in the second image, which may deteriorate the quality of the second image. In some embodiments, the processing device 140 may process the first imaging dataset by compensating the motion difference. The processing device 140 may then reconstruct the second image based on the processed first imaging dataset.

In some embodiments, the image-guided treatment apparatus 110 may include at least one more imaging assembly. For instance, the second ring assembly may include a third radiation source and a second radiation detector. The third radiation source (and/or the second radiation source) in the second ring assembly may deliver a second imaging beam to the object. The second radiation detector in the second ring assembly may detect the second imaging beam to generate a second imaging dataset (e.g., projection data). In some embodiments, the processing device 140 may correct the second image based on the second imaging dataset. For example, the processing device 140 may reconstruct the second image based on the first imaging dataset and the second imaging dataset. As another example, the processing device 140 may reduce the artifacts in the second image based on the second imaging dataset. In some embodiments, the processing device 140 may reconstruct an image based on the imaging dataset(s) acquired by imaging assemblies as illustrated in FIGS. 7 and 8, in combination with additional imaging dataset by another imaging assembly of the image-guided treatment apparatus 110, or by another CT device. For instance, such additional imaging dataset may be acquired by a further imaging assembly of the image-guided treatment apparatus 110. The further imaging assembly may be formed by a radiation source and a radiation detector located in the same ring assembly (e.g., the second ring assembly, the third ring assembly) in which the imaging beam passes through the isocenter thereof.

In some embodiments, the processing device 140 may augment or supplement at least a portion of the first imaging dataset based on data derived from one or more reference images including, for example, a planning CT and/or a previously determined 3D or 4D image (e.g., the first image). Merely by way of example, the processing device 140 may analyze or determine what data are missing based on a trajectory of the imaging assembly (e.g., the second radiation source in the second ring assembly 620 and/or the first radiation detector in the third ring assembly 630); the processing device 140 may determine corresponding data in the reference image(s) that can be used to augment the missing data; and the processing device 140 may insert the corresponding data to supplement the missing data. In some embodiments, in the data augmentation operation, the processing device 140 may use one or more tomographic consistency conditions derived from the first image, so that the image quality of the second image may be improved.

In 913, the treatment assembly (e.g., the first radiation source) may deliver, based on the second image, a treatment beam toward a target portion of the object. The target portion of the object may correspond to the ROI in the second image. The second image may include information related to the ROI or the reference portion, such as the location of the ROI, the location of the reference portion. The treatment assembly may deliver the treatment beam toward the target portion of the object that conforms to the location of the ROI. In some embodiments, the processing device 140 may detect a movement or change of the target portion of the object based on the second image. The processing device 140 may revise the delivery of the treatment beam or the position of the object. For example, the processing device 140 may pause the delivery of the treatment beam, and then adjust the radiation source (e.g., the first radiation source) of the treatment assembly to target at the location of the moved or changed target portion of the object. As another example, the processing device 140 may pause the delivery of the treatment beam, and then adjust the position of the target portion of the object with respect to the treatment beam to make the treatment beam target at the target portion. The processing device 140 (e.g., the control module 504) may adjust the position of the object by moving the object in a table (e.g., the table 114) in the bore of the treatment assembly. After the delivery of the treatment beam or the position of the object is adjusted, the treatment assembly may resume the delivery of the treatment beam. In some embodiments, when detecting the movement or change of the target portion, the treatment assembly may terminate the delivery. In some embodiments, the processing device 140 may generate a notification based on the detected movement or change of the target portion of the object. In some embodiments, the notification may include information of the movement or change of the target portion. The notification may be in a form of text, video, audio, etc.

In some embodiments, the delivery of the treatment beam in 913 and the delivery of the first imaging beam in 907 may be performed simultaneously. In some embodiments, the delivery of the treatment beam in 913 and the delivery of the first imaging beam in 907 may be performed alternately. Therefore, the imaging assembly may track the motion of the target portion of the object while the treatment beam is delivered or from time to time.

In some embodiments, the generation of the second image in 911 may be unnecessary, and accordingly, the treatment beam may be delivered based on at least a portion of the first imaging dataset (or processed first imaging dataset) instead of the second image. Merely by way of example, in 913, the processing device 140 may analyze projection data corresponding to at least a portion of the first imaging dataset or processed first imaging dataset (e.g., compare the projection data with reference projection data) to infer the position/trajectory of the ROI (or the target portion of the object), and deliver the treatment beam based on the position/trajectory of the ROI.

It should be noted that the above description of the process 900 for radiotherapy is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. For example, an operation for adjusting the position of the target portion of the object and/or revising the treatment beam may be added between operations 911 and 913. As another example, the treatment beam may be delivered based on one or more instructions or manipulations of an operator (e.g., a doctor). As a further example, the operations 901 and/or 903 may be omitted.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiation system, comprising:
   a first ring assembly including a first radiation source configured to deliver a treatment beam covering a treatment region of the radiation system, the treatment region being located in a bore of the radiation system;

a second radiation source configured to deliver a first imaging beam covering a first imaging region of the radiation system or a second imaging beam, the second radiation source being mounted rotatably on a second ring assembly, the second ring assembly being located on a first side of the first ring assembly;

a first radiation detector configured to detect at least a portion of the first imaging beam, the first radiation detector being mounted rotatably on a third ring assembly, the third ring assembly being located on a second side of the first ring assembly; and a second radiation detector configured to detect at least a portion of the second imaging beam, the second radiation detector being mounted rotatably on the second ring assembly, wherein the first ring assembly, the second radiation source, and the first radiation detector are positioned such that the treatment region is addressable for the radiation system.

2. The radiation system of claim 1, wherein the first ring assembly defines a first bore, the second ring assembly defines a second bore, the third ring assembly defines a third bore, and the first bore, the second bore, and the third bore constitutes a space to receive an object, and/or the first bore, the second bore, and the third bore are concentric.

3. The radiation system of claim 2, wherein the first radiation detector at least partially extends into the first bore of the first ring assembly.

4. The radiation system of claim 1, wherein the first radiation source is rotatable, and a rotation of the first radiation source is independent of at least one of the second radiation source or the first radiation detector.

5. The radiation system of claim 1, wherein a rotation of the second radiation source is independent of at least one of the first radiation source or the first radiation detector, and/or a rotation of the first radiation detector is independent of at least one of the first radiation source or the second radiation source.

6. The radiation system of claim 1, wherein the second ring assembly is rotatable, and a rotation of the second ring assembly is independent of at least one of the first ring assembly or the third ring assembly.

7. The radiation system of claim 1, wherein the third ring assembly is rotatable, and a rotation of the third ring assembly is independent of at least one of the first ring assembly or the second ring assembly.

8. The radiation system of claim 1, further comprising:
a processing module configured to reconstruct an image or generate projection data based on the at least a portion of the first imaging beam detected by the first radiation detector; and
a control module configured to control operation of the radiation system.

9. The radiation system of claim 8, wherein the processing module reconstructs the image or generates the projection data when the first radiation source delivers the treatment beam.

10. The radiation system of claim 9, wherein:
the processing module, based on the reconstructed image or projection data corresponding to the at least a portion of the first imaging beam detected by the first radiation detector, determines an adjustment; and
the control module, based on the determined adjustment, causes the first radiation source to deliver an adjusted treatment beam or causes a position of an object to be adjusted with respect to the treatment beam.

11. The radiation system of claim 1, wherein the first imaging beam includes diagnostic X-rays, and the second radiation source includes a diagnostic X-ray tube.

12. The radiation system of claim 11, wherein the diagnostic X-ray tube directs the diagnostic X-rays in a substantially diagonal direction towards the first radiation detector.

13. The radiation system of claim 11, wherein the second ring assembly and the third ring assembly rotate synchronously.

14. The radiation system of claim 1, further comprising:
a first position sensor, configured to record a motion of the second ring assembly;
a second position sensor, configured to record a motion of the third ring assembly; and
a processing module configured to:
determine, based on the recorded motion of the second ring assembly and the recorded motion of the third ring assembly, a motion difference between the second ring assembly and the third ring assembly.

15. The radiation system of claim 14, wherein the processing module is further configured to:
acquire, from the first radiation detector, imaging data generated based on the first imaging beam; and
process the imaging data by accounting for or compensating for the motion difference.

16. The radiation system of claim 14, wherein
the motion of the second ring assembly includes at least one of a rotation or a translation of the second ring assembly;
the motion of the third ring assembly includes at least one of a rotation or a translation of the third ring assembly; and
the motion difference between the second ring assembly and the third ring assembly includes at least one of a rotational phase difference or a translational difference between the second ring assembly and the third ring assembly.

17. The radiation system of claim 1, wherein the second radiation source delivers the first imaging beam when the first radiation source delivers the treatment beam, or the delivery of the treatment beam and the delivery of the first imaging beam alternate.

18. The radiation system of claim 1, wherein at least one of the first radiation detector or the second radiation detector is a flat panel detector or a computed tomography detector.

19. The radiation system of claim 18, wherein
the second radiation source is movable between a first position and a second position;
the second radiation source at the first position delivers the first imaging beam toward the first radiation detector in the third ring assembly; and
the second radiation source at the second position delivers the second imaging beam toward the second radiation detector in the second ring assembly.

* * * * *